United States Patent
Winqvist et al.

(10) Patent No.: US 11,564,969 B2
(45) Date of Patent: *Jan. 31, 2023

(54) IMMUNORHELIN COMPOUNDS FOR INTRACELLULAR INFECTIONS

(71) Applicant: ISR IMMUNE SYSTEM REGULATION HOLDING AB (PUBL), Stockholm (SE)

(72) Inventors: Ola Winqvist, Uppsala (SE); Emma Lindh, Knivsta (SE); Robert Wallin, Bålsta (SE); Matt Gregory, Cambridge (GB); Steven Moss, Cambridge (GB)

(73) Assignee: ISR IMMUNE SYSTEM REGULATION HOLDING AB (publ), Stockholm (SE)

( * ) Notice: Subject to any disclaimer, the term of this patent is extended or adjusted under 35 U.S.C. 154(b) by 74 days.

This patent is subject to a terminal disclaimer.

(21) Appl. No.: 16/479,520

(22) PCT Filed: Jan. 19, 2018

(86) PCT No.: PCT/EP2018/051348
§ 371 (c)(1),
(2) Date: Jul. 19, 2019

(87) PCT Pub. No.: WO2018/134373
PCT Pub. Date: Jul. 26, 2018

(65) Prior Publication Data
US 2019/0388497 A1    Dec. 26, 2019

(30) Foreign Application Priority Data

Jan. 20, 2017 (EP) .................................. 17152466

(51) Int. Cl.
| | | |
|---|---|---|
| C07K 7/23 | (2006.01) |
| A61K 38/09 | (2006.01) |
| A61K 31/565 | (2006.01) |
| A61K 31/568 | (2006.01) |
| A61K 31/573 | (2006.01) |
| A61K 38/00 | (2006.01) |

(52) U.S. Cl.
CPC ............ *A61K 38/09* (2013.01); *A61K 31/565* (2013.01); *A61K 31/568* (2013.01); *A61K 31/573* (2013.01); *C07K 7/23* (2013.01); *A61K 38/00* (2013.01)

(58) Field of Classification Search
CPC .... A61K 38/09; A61K 31/565; A61K 31/568; A61K 31/573; A61K 38/00; A61K 45/06; C07K 7/23; A61P 5/30; A61P 5/26; A61P 5/06; A61P 43/00; A61P 37/04; A61P 33/02; A61P 31/10; A61P 31/04
See application file for complete search history.

(56) References Cited

U.S. PATENT DOCUMENTS

| | | |
|---|---|---|
| 7,834,141 B1 | 11/2010 | Siler-Khodr et al. |
| 2004/0152639 A1 | 8/2004 | Siler-Khodr |
| 2004/0235748 A1* | 11/2004 | Igari ...................... A61K 38/09 514/10.3 |
| 2004/0259803 A1 | 12/2004 | Boyd |
| 2005/0043245 A1 | 2/2005 | Siler-Khodr |
| 2011/0129532 A1 | 6/2011 | Ljungblad et al. |
| 2012/0045393 A1 | 2/2012 | Linder et al. |

FOREIGN PATENT DOCUMENTS

| | | |
|---|---|---|
| EP | 1382350 A1 | 1/2004 |
| GB | 2237571 A | 5/1991 |
| JP | 2003-012552 A | 1/2003 |
| JP | 2004-512011 A | 4/2004 |
| JP | 2007-518699 A | 7/2007 |
| JP | 2009-539952 A | 11/2009 |
| JP | 2010-539008 A | 12/2010 |
| WO | 200174377 A1 | 10/2001 |
| WO | 200230435 A1 | 4/2002 |
| WO | WO 2003/051272 A2 | 6/2003 |
| WO | WO 2004/094599 A2 | 11/2004 |
| WO | WO 2004/103271 A3 | 12/2004 |
| WO | 2007144554 A2 | 12/2007 |
| WO | WO 2009/033663 A1 | 3/2009 |
| WO | WO 2009/033701 A1 | 3/2009 |
| WO | 2009145690 A1 | 12/2009 |
| WO | WO 2018/134372 A1 | 7/2018 |

OTHER PUBLICATIONS

Illing et al (Biochemical and Biophysical Research Communications, 1993, 196(2), 745-51) (Year: 1993).*
Millar et al., "Chimeric Analogues of Vertebrate Gonadotropin-releasing Hormones Comprising Substitutions of the Variant Amino Acids in Positions 5, 7, and 8. Characterization of requirements for receptor binding and gonadotropin release in mammalian and avian pituitary gonadotropes," J Biol Chem 1989 264(35):21007-13.
International Search Report of the International Searching Authority for Application No. PCT/EP2018/051348, dated Mar. 23, 2018, 5 pages.
Written Opinion of the International Searching Authority for Application No. PCT/EP2018/051348, dated Mar. 23, 2018, 6 pages.
International Preliminary Report on Patentability for PCT/EP2018/051348, dated Apr. 24, 2019, 17 pages.
CDC, "Types of Fungal Diseases," (https://www.cdc.gov/fungal/diseases/index.htrn1 accessed May 21, 2021), 2 pages.

(Continued)

*Primary Examiner* — Sudhakar Katakam
(74) *Attorney, Agent, or Firm* — Carl A. Morales; Glenn J. Foulds; Fenwick & West LLP

(57) ABSTRACT

The present invention provides immune stimulating peptides (immunorhelins) capable of activating GnRH receptors when administered to animal or human patients or cells. These immunorhelins have utility in treating intracellular bacterial, fungal, and protozoal infections.

Figure 1:
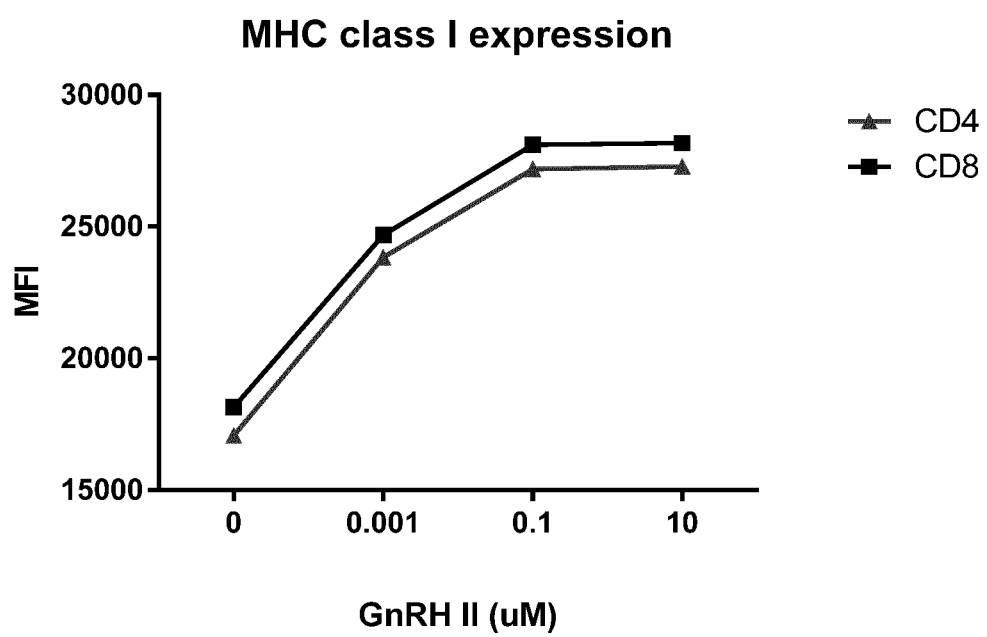

15 Claims, 5 Drawing Sheets
Specification includes a Sequence Listing.

(56) References Cited

OTHER PUBLICATIONS

Doron, "Bacterial infections: Overview," International Encyclopedia of Public Health, 2008:273-282.

Garcia-Gomez, "Role of Sex Steroid Hormones in Bacterial-Host Interactions," Hindawi Publishing Corporation, BioMed Research International vol. 2013, Article ID 928290, 10 pages, http://dx.doi.org/10.1155/2013/928290.

Immunopaedia.org, "Internet archive of 4. MHC & Antigen Presentation," Dec. 8, 2016, Retrieved from internet on Nov. 18, 2021, https://web.archive.org/web/20161208044034/https://www.immunopaedia.org.za/immunology/basics/4-mhc-antigen-presentation/, 8 pages.

Iseda and Matano, "Progress toward prevention and cure of HIV infection" with abridged English translation, AIDS Research Center, National Institute of Infectious Diseases, vol. 33, No. 17, 2015, pp. 2727-2731.

ITH/ISR Immune System Regulation: "An open phase II study in HIV-1 infected untreated male adult patients to evaluate safety and tolerability and the in vivo effects on T cell population and viral load of a GnRH analogue administered by intranasal administration during 28 days when combined with a single intramuscular testosterone depot injection to restore a normal serum testosterone level", Apr. 30, 2014 (Apr. 30, 2014), pp. 1-13, XP055394073.

Limonta et al., "GnRH receptors in cancer: From cell biology to novel targeted therapeutic strategies," *Endocrine Reviews*, Oct. 2012, 33(5):784-811).

National Cancer Institute, "What is Cancer?" retrieved online on Sep. 24, 2021 from https://www.cancer.gov/about-cancer/understanding/what-is-cancer, 8 pages.

National Institute of Health, "Antimicrobial Resistance Threats," (https://www.niaid.nih.gov/research/antirnicrobial-resistance-threats Feb. 11, 2020), 3 pages.

Saussez et al., "Towards neuroimmunotherapy for cancer: the neurotransmitters glutamate, dopamine and GnRH-II augment substantially the ability of T cells of few head and neck cancer patients to perform spontaneous migration, chemotactic migration and migration towards the autologous tumor, and also elevate markedly the expression of CD3zeta and CD3epsilon TCR-associated chains," *Journal of Neural Transmission*, Jul. 2014, 121, pp. 1007-1027, https://doi.org/10.1007/s00702-014-1242-y.

Kamaruzzaman, N. et al., "Targeting the hard to reach: challenges and novel strategies in the treatment of intracellular bacterial infections," *British Journal of Pharmacology*, vol. 174, Issue 14, 2016, pp. 2225-2236.

Overview of Viruses, Merck Manuals, accessed at URL merckmanuals.com/professional/infectious-diseases/viruses/overview-of-viruses, pp. 1-6 (Year: 2019).

\* cited by examiner

IMMUNORHELIN COMPOUNDS FOR INTRACELLULAR INFECTIONS

FIELD OF THE INVENTION

The present invention provides a set of novel peptides capable of stimulating the immune system, named immunorhelins. The invention also provides novel peptides capable of stimulating GnRH receptors on leukocytes. The present invention relates to novel compounds as such and to the compounds for use in medicine, notably in the treatment of intracellular infections. The immunorhelins may also be used as immunomodulating adjuvants in vaccination. The novel GnRH receptor stimulating immunorhelins maximizes the modulating effects of the immune system while minimizing the therapeutically unwanted endocrine effects. The present invention also provides methods for preparing immunorhelins of the invention that have improved properties for use in medicine.

BACKGROUND OF THE INVENTION

Intracellular bacterial, fungal, and protozoal infections are often not diagnosed in healthy individuals as they appear asymptomatic, or because the symptoms are mild enough that the infected individual is not inclined to seek medical assistance. As such, intracellular infections may persist latently or may progress to a disease state. Conditions interfering with normal T cell function usually leads to progression of the disease from a latent infection and intracellular infections such as *Mycobacterium tuberculosis* (Mtb) are a common cause of death in patients where HIV infection has progressed to AIDS. There is thus also a great need in the art for methods and means of treating infections.

Intracellular pathogens such as Mtb have the capacity to hide within intracellular compartments in monocytes and macrophages causing persistent infections. Although Mtb are recognized by $CD4^+$ T helper cells in the lung and an appropriate response is mounted, the system fails to create sterilizing immunity (MacMicking 2012). To escape immune recognition by the host, Mtb have developed a series of mechanism that inhibits recognition of Mtb peptides presented in the MHC class II pocket for $CD4^+$ T helper cells. Toll like receptor 2 has been demonstrated to be inhibited by Mtb, which in turn inhibits IFN-γ induced MHC class II expression (Noss 2001). In addition, data suggest that Mtb has the capacity to inhibit phagosome processing and maturation, possibly by an invariant chain associated mechanism (Ramachandra 2001). Therefore, the normal antigen processing, loading and presentation of MHC class II peptides derived from Mtb is impaired due to Mtb produced immune escape factors.

The endosomal lysosomal pathway is designed to take up pathogens, process them into 12-15 aa long peptides, peptides, that after the removal of the Invariant chain peptide CLIP by HLA-DM, are loaded into the MHC class II pocket. The antigen loading is followed by transport of the MHC class II-peptide complex to the cell surface for presentation for the specific T cell receptor of $CD4^+$ T helper cells (Roche 2015). Recently the Mtb expressed protein EsxH has been reported to directly inhibit the endosomal sorting complex required for transport (ESCRT) machinery (Portal-Celhay 2016). EsxH inhibits the ability of antigen presenting monocytes and macrophages to activate $CD4^+$ T helper cells. Since intact ESCRT machinery seems necessary for antigen processing, presentation and activation of T cells, EsxH is the link that explains Mtb induced immune escape by intervening with the MHC class II pathway.

The importance of MHC class II presentation has also been demonstrated in patients with primary immunodeficiencies (PID). PID patients with defects in the IFN-γ circuit, involving IFNGR, IL-12 have an increased of acquiring TBC and atypical mycobacterial infections. Since MHC class II expression is dependent and regulated by IFN-γ expression defects in the IFN-γ circuit will result in additionally decreased MHC class II expression and a poor activation of $CD4^+$ T helper cells.

Protozoa such as *Toxoplasma gondii* have developed a mechanism to avoid immune recognition by hiding intracellularly as an obligate intracellular parasite. The mechanism involves interference with MHC class II expression and thus diminish the amount of Toxoplasma *gondii* to be presented for specific $CD4^+$ T helper cells. The detailed mechanism is dependent on soluble proteins expressed by *Toxoplasma gondii* that inhibit IFN-gamma induced expression of MHC class II (Leroux 2015).

Furthermore, it has been demonstrated that different fungal infections are dependent on MHC class II expression. *Cryptococos neoformans* may cause life threatening brain infections in patients with immunodeficiencies including HIV. Work in a mouse model of *Cryptococos neoformans* has demonstrated that the activation of microglial cells and their upregulation of MHC class II, in an IFN-gamma dependent manner, is critical for survival (Zhou 2007).

Therefore, to overcome the immune escape mechanisms induced by Mtb and other intracellular bacteria, protozoa such as *Toxoplasma gondii*, or fungi exemplified by *Cryptococus* an increased expression of MHC class II and MHC class I on the cell surface of monocytes, macrophages, microglia or other infected cells is likely beneficial for immune recognition and elimination of the pathogen

Introduction to the Invention

GnRH I (also known as gonadotropin releasing hormone or LHRH), is a decapeptide with the structure pyroGlu-His-Trp-Ser-Tyr-Gly-Leu-Arg-Pro-Gly-NH$_2$. It is produced as a 92 amino-acid propeptide which is modified post-translationally to form the final peptide with pyroglutamic acid at the amino terminus and a carboxamide at the carboxyl terminus. It has long been known that it is responsible for release of FSH and LH from the anterior pituitary gland, and is normally released from the hypothalamus in a pulsative manner. Supraphysiological levels of GnRH I induce an immediate increase of FSH and LH secretion, soon followed by inhibition of FSH and LH secretion. This is due to the fact that high levels of GnRH I have an inhibitory effect on the type I GnRH receptors of the anterior pituary gland. Continuous administration of GnRH I at high unphysiological levels thus induces pharmacological castration (Fink 1998). A large number of GnRH I agonists and antagonists have been synthesized for use in therapeutic areas such as hormone sensitive cancer. Initially, salts of GnRH I were used therapeutically (such as gonadorelin hydrochloride and gonadorelin diacetate tetrahydrate). Further drug discovery and development led to the clinical use of a wide variety of agents, including buserelin, triptorelin, nafarelin, histrelin and leuprorelin, each of which has improvements over gonadorelin such as extended half-life and super-agonism of the type I GnRH receptor.

It has been reported that GnRH I not only exhibits hormonal effects but also may stimulate the immune system (Jacobson and Ansari 2004). McClean and McCluggage (McClean and McCluggage 2003) observed massive infiltration of small mature lymphocytes in uterine leiomyomas after preoperative treatment with a type I GnRH receptor agonist. Bardsley et al (Bardsley 1998) made the same observation, indicating a stimulatory effect on migration of GnRH I on the immune cells. Reports have been made on chronic plasma cell endometritis in hysterectomy specimens from HIV-infected women in a retrospective analysis (Kerr-Layton 1998), and on elevated levels of FSH and LH (hypergonadotropic) in HIV-infected men (Arver 1999 and Brockmeyer 2000). By administering GnRH I to diabetes-prone BB rats exhibiting an AIDS-like lymphocyte profile the CD4 T-lymphocyte numbers was increased (Jacobson 1999).

WO 2009/145690 A1 teaches us that GnRHs activate and upregulate MHC class I on T cells with the notion that HIV infected CD4 T cells down regulate MHC class I due to the HIV encoded protein Nef therefore avoiding recognition (Lubben et al., 2007

In humans, two variants of GnRH peptide exist, GnRH I and GnRH II, coded for by different genes. The structure of GnRH II is pyroGlu-His-Trp-Ser-<u>His</u>-Gly-<u>Trp</u>-<u>Tyr</u>-Pro-Gly-$NH_2$ (differences from GnRH I underlined). GnRH II is a nonhypothalamic form primarily produced outside the brain, and has been suggested to be involved in the non-endocrine aspects of the GnRH system (White 1998). Surprisingly, we found an effect of GnRH II stimulation on the MHC class I expression on T cells demonstrating that GnRH II directly activates these cells (FIG. 1).

Figure 4:
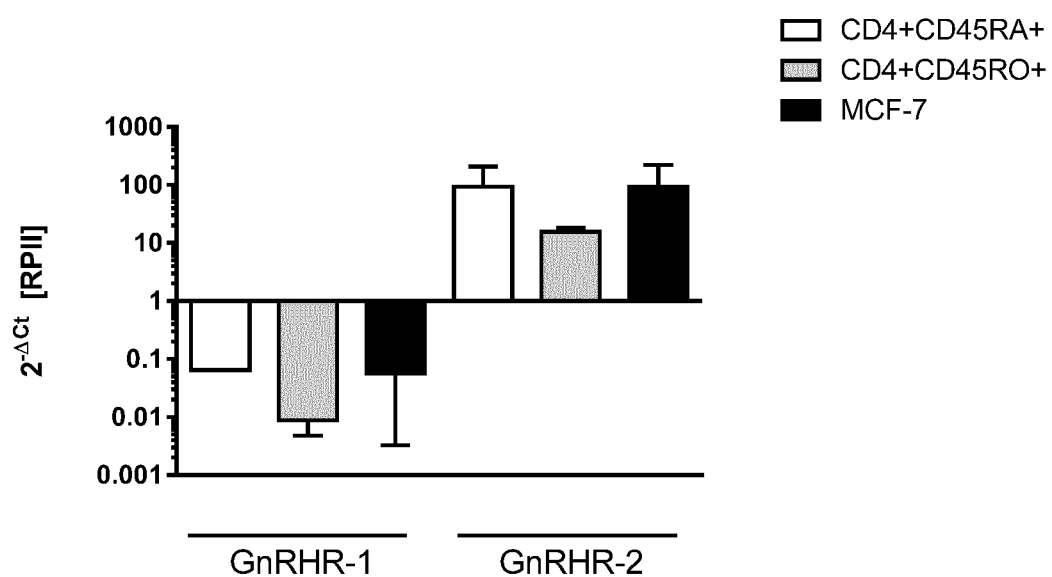

Unlike other mammals, only one conventional human GnRH receptor has been described, the type I GnRH receptor. The type II GnRH receptor homologue is present on chromosome 1q12 gene in humans but contains a frame shift and a stop codon and is believed not to be functionally expressed (Morgan 2003). Surprisingly, our findings suggest that the type II GnRH receptor is indeed expressed on T cells as they respond to GnRH stimulation by increased MHC class I expression (FIG. 1). These functional findings were substantiated by qPCR analysis where we could demonstrate expression of the type II GnRH receptor mRNA. In addition, the relative expression level of the type II GnRH receptor was higher compared to the expression levels of the type I GnRH receptor on naive and memory T cells (FIG. 4). Thus, we have identified that the expression of the type II GnRH receptor is the dominant receptor expressed on T cells, functionally responsive to GnRH stimulus.

We have also discovered that GnRH I analogs may activate T cells leading to MHC class I expression. In a recent clinical trial using the GnRH I analog Buserelin as treatment for HIV, HIV infected men were provided with sex hormone substitution to minimize the endocrine effects of GnRH I. These effects are mediated by GnRH I binding to pituitary type I GnRH receptors, causing decreased testosterone production and subsequently impotence. It is very likely that GnRH I in addition to its endocrine effects cross-signal and stimulate the immune system by binding to the type II GnRH receptor on T cells when high castrating levels of GnRH analogues are used. Interestingly, GnRH I binding to receptors expressed in breast cancer cells displays a low binding affinity (Kd, $1.6$-$3.0 \times 10(-6)$ M), whereas central pituitary binding of GnRH I displays a 1000-fold higher affinity (Kd, $4.8 \times 10(-9)$ M) (Eidne 1987).

It is likely that the difference in binding affinity of GnRH I and GnRH II peptides reflects the expression of type I GnRH receptors specialised for GnRH I binding on pituitary cells, whereas peripheral cells may have dominated expression of type II GnRH receptor and therefore low affinity and an "off target" effect of GnRH I binding. Thus, our unexpected finding that the type II GnRH receptor is the dominating receptor on T cells is novel and may explain the receptor physiology of GnRH I and GnRH II. Therefore, by using GnRH II-like peptides in the treatment of HIV the endocrine effect should be minimized and the immune stimulation effect isolated and enhanced.

DESCRIPTION OF THE INVENTION

Based on these discoveries, the inventors have made GnRH II-like peptides, termed immunorhelins, in order to optimise immune stimulating effects and minimize the effect on the hormonal system. These immunorhelins have use in stimulating MHC class I capable of leading to an immune response clearing infectious agents, such as intracellular infections, and in treating or co-treating HIV or cancer. Therefore, several GnRH II-like peptides are disclosed which have potent binding to type II GnRH receptors but preferably weaker binding to type I GnRH receptors, leading to a comparable or stronger MHC class I response, but a weaker 'off-target' effect on hormone stimulation or inhibition. In the case that GnRH II-like peptides of the invention also bind and activate Type I GnRH receptors thereby stimulating endocrine signalling, the compounds of the present invention may therefore be administered together with one or more natural, semi-synthetic or synthetic sex hormones to counter the endocrine effects of GnRH II-like peptides, e.g. testosterone or oestrogen depending on the hormonal status of the patient. In an adult male person the natural, semi-synthetic or synthetic sex hormone is testosterone or an agent having a corresponding hormonal effect. In an adult female person the natural, semi-synthetic or synthetic sex hormone is oestradiol or an agent having a corresponding hormonal effect, in particular in combination with a progestogen. The latter is added to avoid the development of endometrial cancer in the female and to avoid vaginal bleedings. Hysterectomized women, however, do not benefit from the addition of progestogen.

Viral peptides emerge in the cytosol and are targeted to the proteosome followed by processing and transport (TAP1 and TAP2) into the endoplasmatic reticulum where digested HIV peptides are added into the MHC class I peptide, followed by transport to the cell surface for presentation.

Figure 2A:
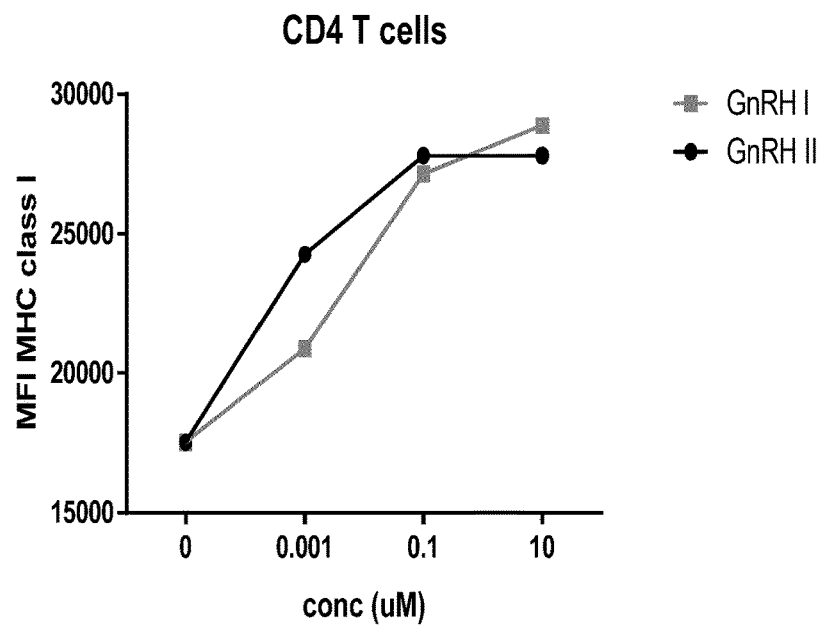
Figure 2B:
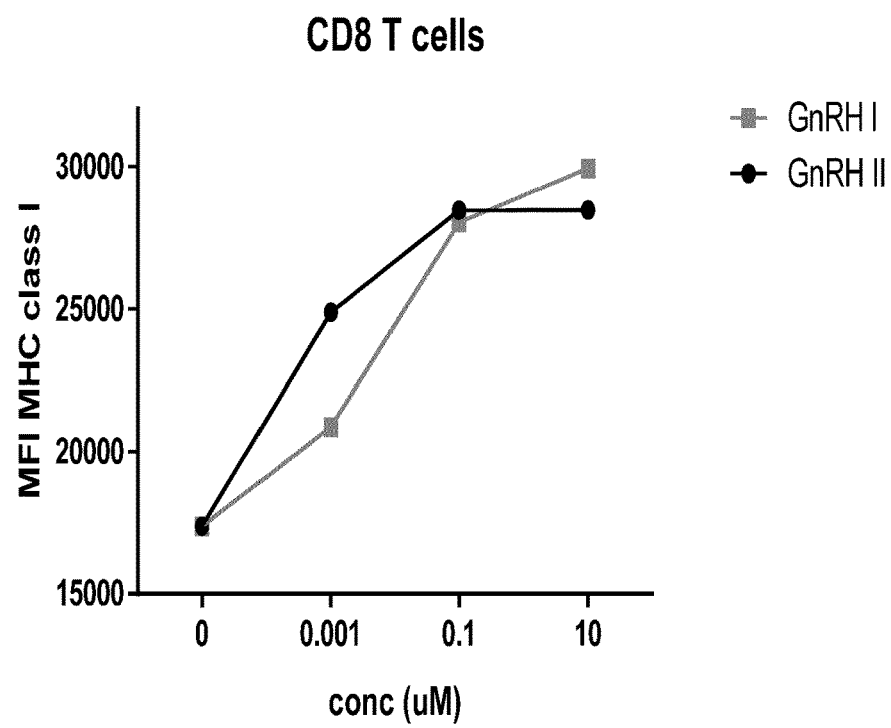

In contrast to the teaching of WO 2009/145690 A1 and in known art, intracellular bacteria are residents of the endosomal lysosmal pathway, a pathway normally not accessible for MHC class I in normal cells such as in T cells. However, in the present invention we demonstrate for the first time that GnRHs can upregulate MHC class I on antigen presenting cells (APCs) such as CD14+ monocytes (FIG. 2). APCs have the unique capability of cross presentation, i.e. they can present antigens from the endosomal lysosmal pathway into the MHC class I pocket, for activation of CD8+ T cells. This finding was surprising and suggests that intracellular bacteria such as *M. tuberculosis* which reside and hides in the endosomal lysosmal pathway of APCs. Thus, treating *M. tuberculosis* infected individuals with GnRHs will activate and stimulate APCs to initiate MHC class I upregulation by the cross-presentation pathway leading to recognition of *M. tuberculosis* peptides by CD8+ T cells and elimination of infected APCS.

The present invention also provides a method for treating intracellular infections such as infections by bacteria, protozoa and fungi by use of one or more GnRH analogs. Intracellular bacteria to be treated include *Mycobacterium tuberculosis*, Mycobacteria causing atypical disease, *Mycobacterium avium* and *M. intracellulare* (also known as *Mycobacterium avium-intracellulare* complex, or MAC), *M. kansasii, M. marinum, M. fortuitum, M. gordinae, Mycoplasma pneumoniae, M. genitalium, M. hominis, Ureaplasma urealyticum, U. parvum, Chlamydophila pneumoniae*, and *Salmonella typhimurium*. Intracellular protozoa include *Toxoplasma gondii, Plasmodium falciparum, P. vivax, Trypanosoma cruzi, Cryptosporidium*, and *Leishmania*. Intracellular fungi include *Histoplasma capsulatum, Cryptococcus neoformans*, and *Encephalitozoon cuniculi*.

The present invention provides peptide-based analogues of human GnRH II.

The compounds of the invention is contemplated to induce improved MHC II and/or MHC I antigen presentation, which make them useful in the treatment of intracellular bacterial, fungal, and protozoal infections. The present invention further provides a method for treating intracellular infection which comprises administration of an unphysiological amount of GnRH or a GnRH analog, and preferably also administering a sex hormone Thus, in one aspect of the invention there is provided a peptide of Formula (I):

$R_2=$

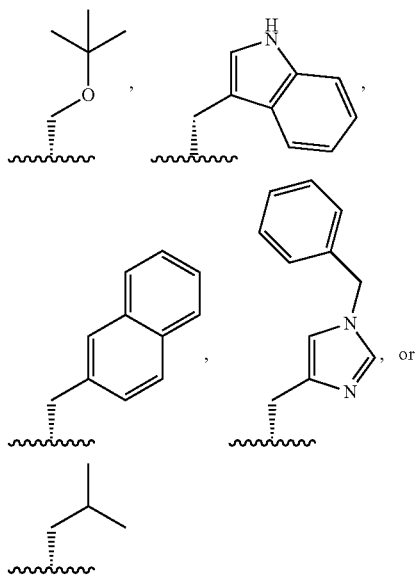

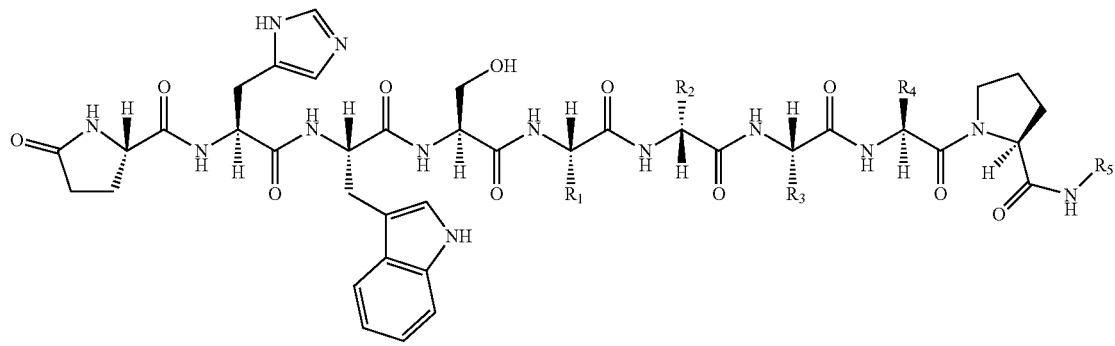

(I)

or a pharmaceutically acceptable salt thereof, and wherein $R_1=$ $R_3=$

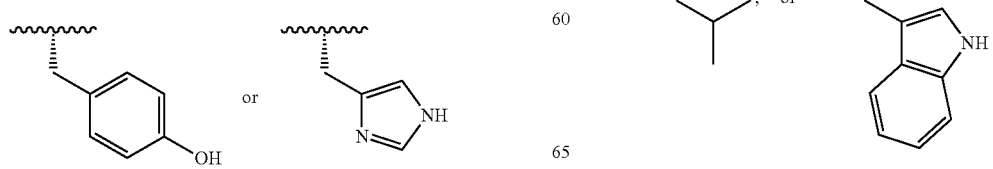

R₄=

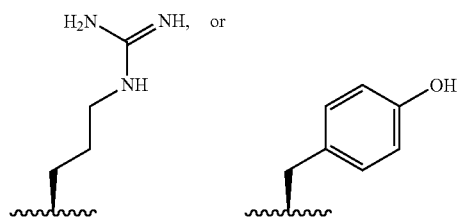

R₅=Me, Et, CH₂CF₃, iPr, nPr, nBu, iBu, sBu, tBu, cyclopropyl, CH₂CONH₂, or NHCONH₂

Formula I regarding the compounds of the invention can also be expressed as: pGlu-His-Trp-Ser-AA₁-AA₂-AA₃-AA₄-Pro-X, wherein:
AA₁ is selected from His and Tyr
AA₂ is selected from D-Ser(OtBu), D-Trp, D-Nal, D-Bhi, and D-Leu
AA₃ is selected from Leu and Trp
AA₄ is selected from Arg and Tyr
X is selected from —NHMe, —NHEt, —NHCH₂CF₃, —NHiPr, —NHnPr, —NHnBu, —NHiBu, —NHsBu, —NHtBu, —NHcyclopropyl, —NH—NH—CONH₂ and —NHCH₂CONH₂

The invention does not include the following compounds of formula (I):

| Proviso | R1 | R2 | R3 | R4 | R5 |
|---|---|---|---|---|---|
| P1 | imidazole-CH₂- (His) | -CH₂-O-tBu | indole-CH₂- (Trp) | 4-hydroxybenzyl (Tyr) | CH₂CONH₂ |
| P2 | imidazole-CH₂- (His) | indole-CH₂- (Trp) | isobutyl (Leu) | guanidino-propyl (Arg) | CH₂CONH₂ |
| P3 | 4-hydroxybenzyl (Tyr) | indole-CH₂- (Trp) | indole-CH₂- (Trp) | guanidino-propyl (Arg) | CH₂CONH₂ |
| P4 | imidazole-CH₂- (His) | indole-CH₂- (Trp) | indole-CH₂- (Trp) | guanidino-propyl (Arg) | CH₂CONH₂ |
| P5 | 4-hydroxybenzyl (Tyr) | indole-CH₂- (Trp) | indole-CH₂- (Trp) | 4-hydroxybenzyl (Tyr) | CH₂CONH₂ |

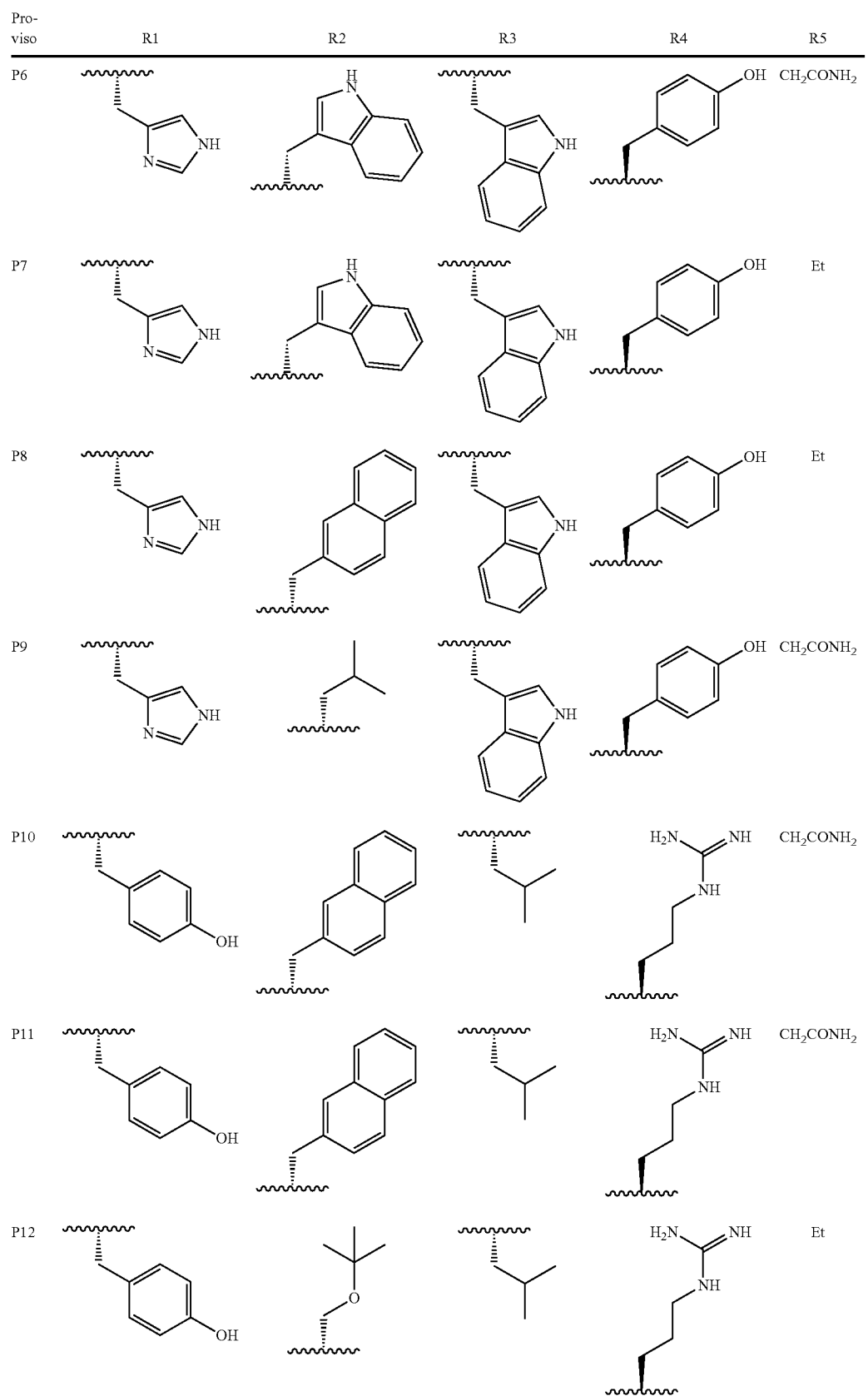

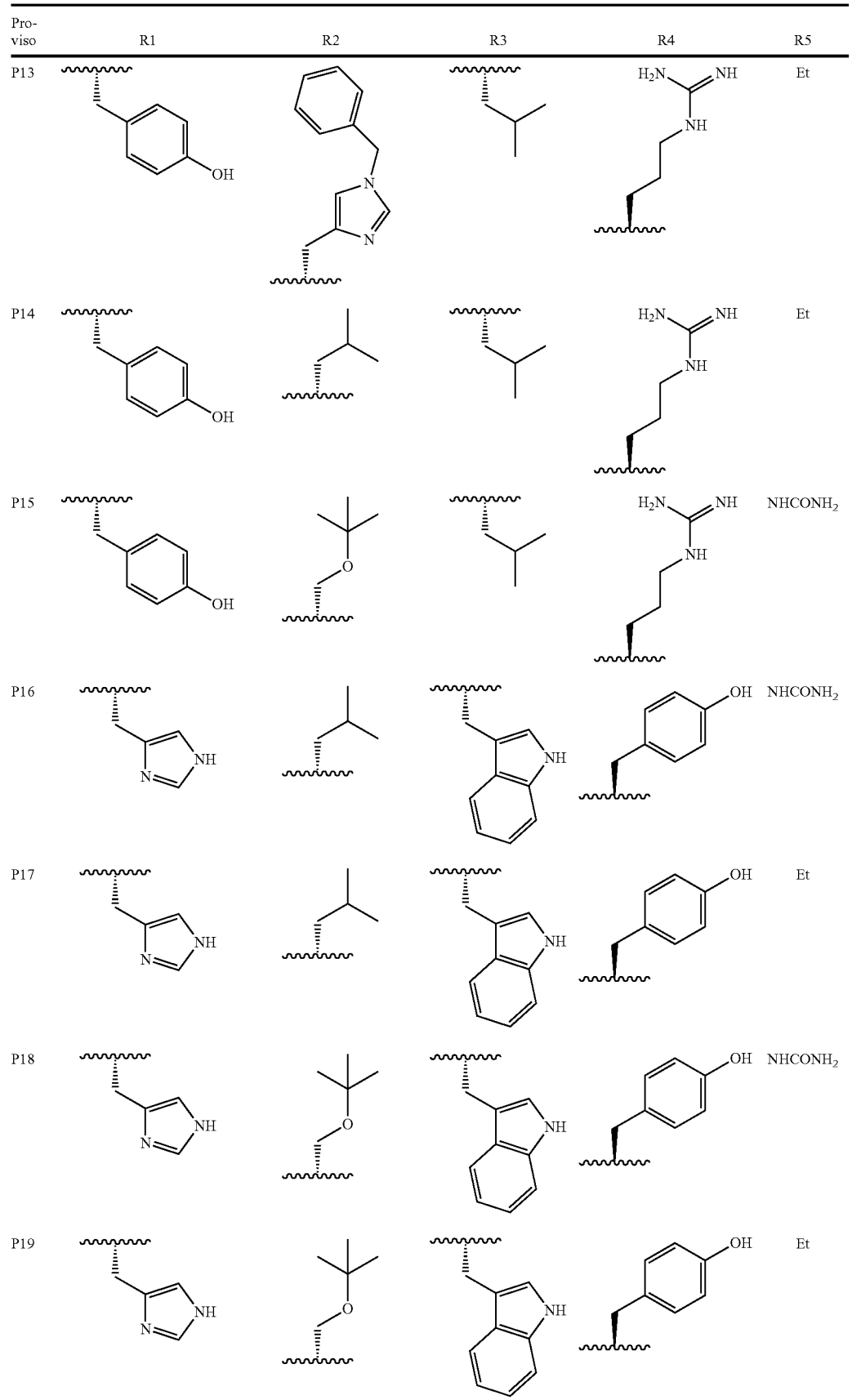

| Proviso | R1 | R2 | R3 | R4 | R5 |
|---|---|---|---|---|---|
| P20 | imidazole (His) | indole (Trp) | indole (Trp) | phenol-OH (Tyr) | NHCONH₂ |
| P21 | imidazole (His) | indole (Trp) | indole (Trp) | phenol-OH (Tyr) | Et |

Disclaimed are compounds of formula (I) expressed as: pGlu-His-Trp-Ser-AA₁-AA₂-AA₃-AA₄-Pro-X, where AA₁ is His, AA₃ is Trp, AA₄ is Tyr and AA₂ is selected from D-Leu, D-tBu-Ser and D-Trp, and X is —NHEt or NH—NH—CONH2.

The compounds P1-P15 excluded from the invention can also be expressed as follows:

P1.  pGlu-His-Trp-Ser-His-D-Ser(tBu)-Trp-Tyr-Pro-Gly-NH₂

P2. pGlu-His-Trp-Ser-His-D-Trp-Leu-Arg-Pro-Gly-NH₂

P3. pGlu-His-Trp-Ser-Tyr-D-Trp-Trp-Arg-Pro-Gly-NH₂

P4. pGlu-His-Trp-Ser-His-D-Trp-Trp-Arg-Pro-Gly-NH₂

P5. pGlu-His-Trp-Ser-Tyr-D-Trp-Trp-Tyr-Pro-Gly-NH₂

P6. pGlu-His-Trp-Ser-His-D-Trp-Trp-Tyr-Pro-Gly-NH₂

P7. pGlu-His-Trp-Ser-His-D-Trp-Trp-Tyr-Pro-NHEt

P8. pGlu-His-Trp-Ser-His-D-Nal-Trp-Tyr-Pro-NHEt

P9. pGlu-His-Trp-Ser-His-D-Leu-Trp-Tyr-Pro-Gly-NH₂

P10. pGlu-His-Trp-Ser-Tyr-D-Trp-Leu-Arg-Pro-Gly-NH₂

P11. pGlu-His-Trp-Ser-Tyr-D-Nal-Leu-Arg-Pro-Gly-NH₂

P12. pGlu-His-Trp-Ser-Tyr-D-Ser(tBu)-Leu-Arg-Pro-NHEt

P13. pGlu-His-Trp-Ser-Tyr-D-Bhi-Leu-Arg-Pro-NHEt

P14. pGlu-His-Trp-Ser-Tyr-D-Leu-Leu-Arg-Pro-NHEt

P15.  pGlu-His-Trp-Ser-Tyr-D-Ser(tBu)-Leu-Arg-Pro-NHNHCONH₂

An interesting selection of compounds of the invention is compounds of Formula (I), or a pharmaceutically acceptable salt thereof, and wherein:

| Group | Type I | Type II |
|---|---|---|
| R₁ | 4-hydroxybenzyl (Tyr) | imidazolylmethyl (His) |
| R₃ | isobutyl (Leu) | indol-3-ylmethyl (Trp) |
| R₄ | guanidinopropyl (Arg) | 4-hydroxybenzyl (Tyr) | and wherein at least one of R₁, R₃ and R₄ are selected from type II, and those of R₁, R₃ and R₄ which are not selected from type II, are selected from Type I, wherein R₂= tert-butoxymethyl (Ser(tBu)), indol-3-ylmethyl (Trp),

-continued

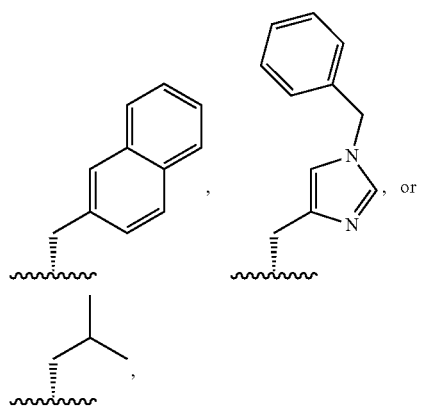

and wherein $R_5$=Me, Et, $CH_2CF_3$, iPr, nPr, nBu, iBu, sBu, tBu, cyclopropyl or, $CH_2CONH_2$ The selection of compounds can also be expressed as:
pGlu-His-Trp-Ser-$AA_1$-$AA_2$-$AA_3$-$AA_4$-Pro-X,
wherein $AA_1$, $AA_2$, $AA_3$, $AA_4$ and X are as defined above and wherein at least one of $AA_1$, $AA_3$ and $AA_4$ is selected from His, Trp and Tyr; the remaining $AA_1$, $AA_3$ and $AA_4$ is selected from Tyr, Leu, Arg and with exclusion of the compounds P1-P15 as specified above and those other compounds disclaimed in claim 1.

In an embodiment, two or three of $R_1$, $R_3$ and $R_4$ are selected from type II according to the list above, and the remaining $R_1$, $R_3$ and $R_4$ are selected from type I.

In an embodiment one of $R_1$, $R_3$ and $R_4$ is selected from Type I according to the list above and two of $R_1$, $R_3$ and $R_4$ are selected from type II according to the list above.
and with exclusion of the compounds P1-P21 as specified above.

Specific compounds according to the invention include:

| Compound no. | R1 | R2 | R3 | R4 | R5 |
|---|---|---|---|---|---|
| 1 | | | | | $CH_2CONH_2$ |

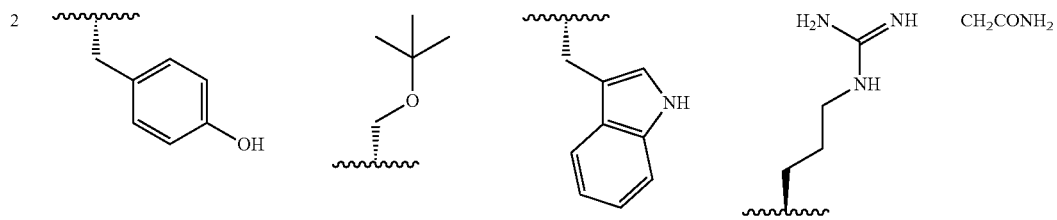

pGlu-His-Trp-Ser-His-D-Ser(tBu)-Leu-Arg-Pro-Gly-amide,

| 2 | | | | | $CH_2CONH_2$ |

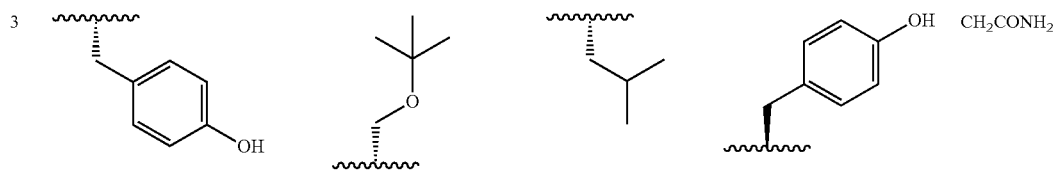

pGlu-His-Trp-Ser-Tyr-D-Ser(tBu)-Trp-Arg-Pro-Gly-amide

| 3 | | | | | $CH_2CONH_2$ | pGlu-His-Trp-Ser-Tyr-D-Ser(tBu)-Leu-Tyr-Pro-Gly-amide

| 4 | | | | | $CH_2CONH_2$ |

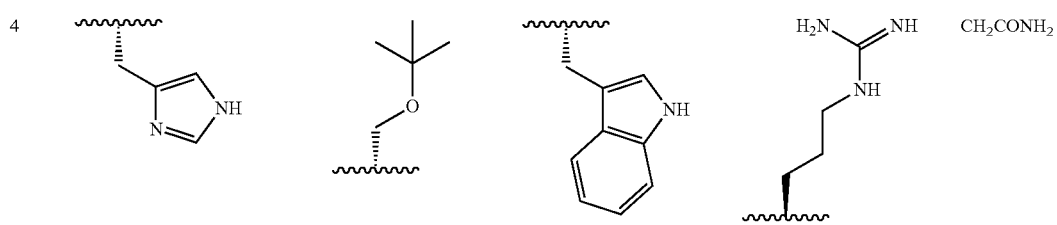

pGlu-His-Trp-Ser-His-D-Ser(tBu)-Trp-Arg-Pro-Gly-amide

-continued

| Compound no. | R1 | R2 | R3 | R4 | R5 |
|---|---|---|---|---|---|
| 5 | imidazole-CH₂- (His) | -CH₂-O-C(CH₃)₃ (Ser(tBu)) | isobutyl (Leu) | 4-hydroxybenzyl (Tyr) | CH₂CONH₂ | pGlu-His-Trp-Ser-His-D-Ser(tBu)-Leu-Tyr-Pro-Gly-amide

| 6 | imidazole-CH₂- (His) | -CH₂-O-C(CH₃)₃ (Ser(tBu)) | isobutyl (Leu) | guanidinopropyl (Arg) | Et | pGlu-His-Trp-Ser-His-D-Ser(tBu)-Leu-Arg-Pro-NHEt

| 7 | 4-hydroxybenzyl (Tyr) | -CH₂-O-C(CH₃)₃ (Ser(tBu)) | indol-3-ylmethyl (Trp) | 4-hydroxybenzyl (Tyr) | CH₂CONH₂ | pGlu-His-Trp-Ser-Tyr-D-Ser(tBu)-Trp-Tyr-Pro-Gly-amide

| 8 | 4-hydroxybenzyl (Tyr) | -CH₂-O-C(CH₃)₃ (Ser(tBu)) | indol-3-ylmethyl (Trp) | guanidinopropyl (Arg) | Et | pGlu-His-Trp-Ser-Tyr-D-Ser(tBu)-Trp-Arg-Pro-NHEt

| 9 | 4-hydroxybenzyl (Tyr) | -CH₂-O-C(CH₃)₃ (Ser(tBu)) | isobutyl (Leu) | 4-hydroxybenzyl (Tyr) | Et | pGlu-His-Trp-Ser-Tyr-D-Ser(tBu)-Leu-Tyr-Pro-NHEt

| 10 | imidazole-CH₂- (His) | -CH₂-O-C(CH₃)₃ (Ser(tBu)) | indol-3-ylmethyl (Trp) | guanidinopropyl (Arg) | Et | pGlu-His-Trp-Ser-His-D-Ser(tBu)-Trp-Arg-Pro-NHEt

-continued

| Compound no. | R1 | R2 | R3 | R4 | R5 |
|---|---|---|---|---|---|
| 11 | (imidazol-4-yl-methyl) | (tBuO-CH2-) | (isobutyl) | (4-hydroxybenzyl) | Et | pGlu-His-Trp-Ser-His-D-Ser(tBu)-Leu-Tyr-Pro-NHEt

| 12 | (4-hydroxybenzyl) | (tBuO-CH2-) | (indol-3-yl-methyl) | (4-hydroxybenzyl) | Et | pGlu-His-Trp-Ser-Tyr-D-Ser(tBu)-Trp-Tyr-Pro-NHEt

| 13 | (imidazol-4-yl-methyl) | (tBuO-CH2-) | (indol-3-yl-methyl) | (4-hydroxybenzyl) | Et | pGlu-His-Trp-Ser-His-D-Ser(tBu)-Trp-Tyr-Pro-NHEt

| 14 | (4-hydroxybenzyl) | (indol-3-yl-methyl) | (isobutyl) | (4-hydroxybenzyl) | CH2CONH2 | pGlu-His-Trp-Ser-Tyr-D-Trp-Leu-Tyr-Pro-Gly-amide

| 15 | (4-hydroxybenzyl) | (indol-3-yl-methyl) | (isobutyl) | (guanidinopropyl) | Et | pGlu-His-Trp-Ser-Tyr-D-Trp-Leu-Arg-Pro-NHEt

| 16 | (imidazol-4-yl-methyl) | (indol-3-yl-methyl) | (isobutyl) | (4-hydroxybenzyl) | CH2CONH2 | pGlu-His-Trp-Ser-His-D-Trp-Leu-Tyr-Pro-Gly-amide

-continued

| Compound no. | R1 | R2 | R3 | R4 | R5 |
|---|---|---|---|---|---|
| 17 | imidazole (His) | indole (Trp) | isobutyl (Leu) | guanidinobutyl (Arg) | Et | pGlu-His-Trp-Ser-His-D-Trp-Leu-Arg-Pro-NHEt

| 18 | phenol (Tyr) | indole (Trp) | indole (Trp) | guanidinobutyl (Arg) | Et | pGlu-His-Trp-Ser-Tyr-D-Trp-Trp-Arg-Pro-NHEt

| 19 | phenol (Tyr) | indole (Trp) | isobutyl (Leu) | phenol (Tyr) | Et | pGlu-His-Trp-Ser-Tyr-D-Trp-Leu-Tyr-Pro-NHEt

| 20 | imidazole (His) | indole (Trp) | indole (Trp) | guanidinobutyl (Arg) | Et | pGlu-His-Trp-Ser-His-D-Trp-Trp-Arg-Pro-NHEt

| 21 | imidazole (His) | indole (Trp) | isobutyl (Leu) | phenol (Tyr) | Et | pGlu-His-Trp-Ser-His-D-Trp-Leu-Tyr-Pro-NHEt

| 22 | phenol (Tyr) | indole (Trp) | indole (Trp) | phenol (Tyr) | Et | pGlu-His-Trp-Ser-Tyr-D-Trp-Trp-Tyr-Pro-NHEt

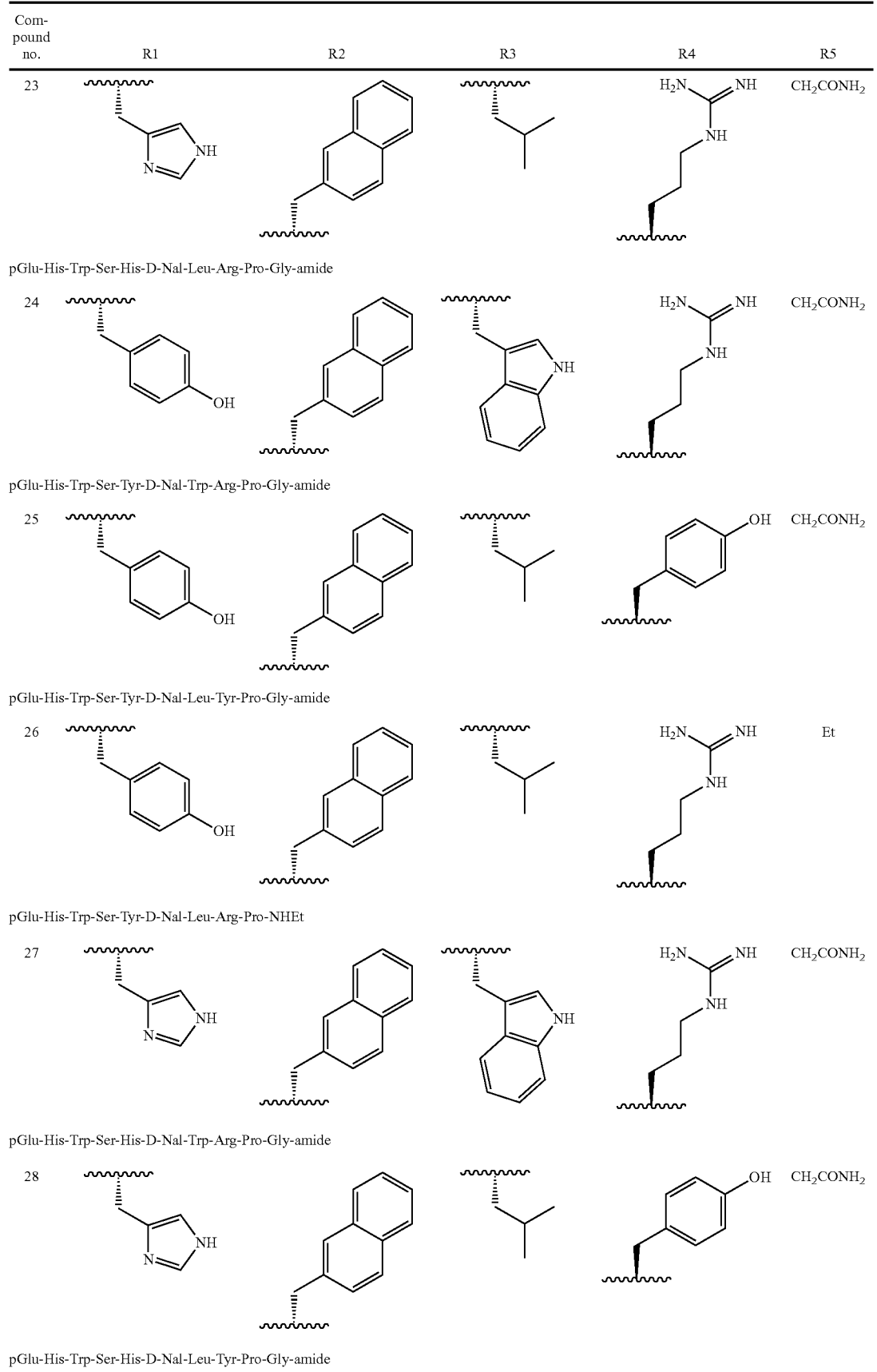

-continued
| Compound no. | R1 | R2 | R3 | R4 | R5 |
|---|---|---|---|---|---|
| 29 | 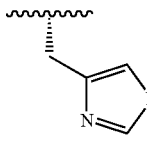 | 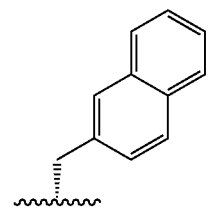 | 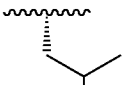 | 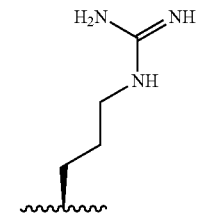 | Et |
pGlu-His-Trp-Ser-His-D-Nal-Leu-Arg-Pro-NHEt,
| 30 | 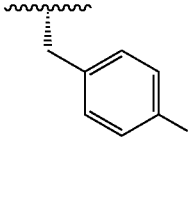 | 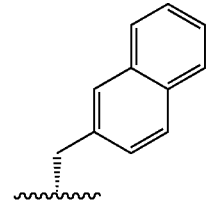 | 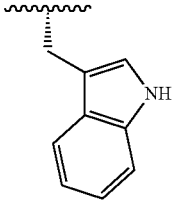 | 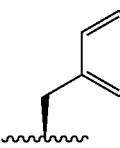 | $CH_2CONH_2$ |
pGlu-His-Trp-Ser-Tyr-D-Nal-Trp-Tyr-Pro-Gly-amide
| 31 | 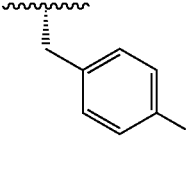 | 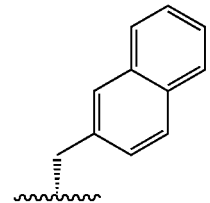 | 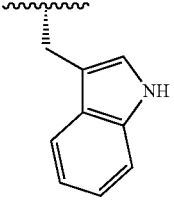 | 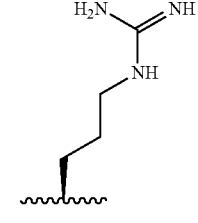 | Et |
pGlu-His-Trp-Ser-Tyr-D-Nal-Trp-Arg-Pro-NHEt
| 32 | 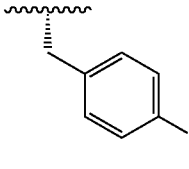 | 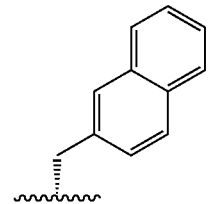 | 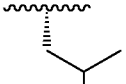 | 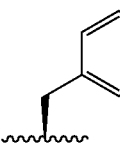 | Et |
pGlu-His-Trp-Ser-Tyr-D-Nal-Leu-Tyr-Pro-NHEt
| 33 | 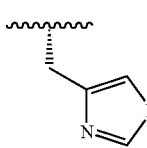 | 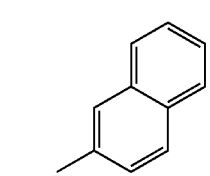 | 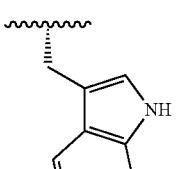 | 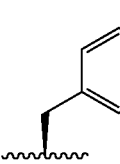 | $CH_2CONH_2$ |
pGlu-His-Trp-Ser-His-D-Nal-Trp-Tyr-Pro-Gly-amide -continued

| Compound no. | R1 | R2 | R3 | R4 | R5 |
|---|---|---|---|---|---|
| 34 | imidazole (His) | 2-naphthylmethyl (Nal) | indole (Trp) | guanidinobutyl (Arg) | Et | pGlu-His-Trp-Ser-His-D-Nal-Trp-Arg-Pro-NHEt

| 35 | imidazole (His) | 2-naphthylmethyl (Nal) | isobutyl (Leu) | 4-hydroxybenzyl (Tyr) | Et | pGlu-His-Trp-Ser-His-D-Nal-Leu-Tyr-Pro-NHEt

| 36 | 4-hydroxybenzyl (Tyr) | 2-naphthylmethyl (Nal) | indole (Trp) | 4-hydroxybenzyl (Tyr) | Et | pGlu-His-Trp-Ser-Tyr-D-Nal-Trp-Tyr-Pro-NHEt

| 37 | imidazole (His) | isobutyl (Leu) | isobutyl (Leu) | guanidinobutyl (Arg) | CH$_2$CONH$_2$ | pGlu-His-Trp-Ser-His-D-Leu-Leu-Arg-Pro-Gly-amide

| 38 | 4-hydroxybenzyl (Tyr) | isobutyl (Leu) | indole (Trp) | guanidinobutyl (Arg) | CH$_2$CONH$_2$ | pGlu-His-Trp-Ser-Try-D-Leu-Trp-Arg-Pro-Gly-amide

| 39 | 4-hydroxybenzyl (Tyr) | isobutyl (Leu) | isobutyl (Leu) | 4-hydroxybenzyl (Tyr) | CH$_2$CONH$_2$ | pGlu-His-Trp-Ser-Tyr-D-Leu-Leu-Tyr-Pro-Gly-amide

-continued

| Compound no. | R1 | R2 | R3 | R4 | R5 |
|---|---|---|---|---|---|
| 40 | imidazole-CH2- (His) | isobutyl (Leu) | indole-CH2- (Trp) | -(CH2)3-NH-C(=NH)-NH2 (Arg) | CH2CONH2 | pGlu-His-Trp-Ser-His-D-Leu-Trp-Arg-Pro-Gly-amide

| 41 | imidazole-CH2- (His) | isobutyl (Leu) | isobutyl (Leu) | 4-hydroxybenzyl (Tyr) | CH2CONH2 | pGlu-His-Trp-Ser-His-D-Leu-Leu-Tyr-Pro-Gly-amide

| 42 | imidazole-CH2- (His) | isobutyl (Leu) | isobutyl (Leu) | -(CH2)3-NH-C(=NH)-NH2 (Arg) | Et | pGlu-His-Trp-Ser-His-D-Leu-Leu-Arg-Pro-NHEt

| 43 | 4-hydroxybenzyl (Tyr) | isobutyl (Leu) | indole-CH2- (Trp) | 4-hydroxybenzyl (Tyr) | CH2CONH2 | pGlu-His-Trp-Ser-Tyr-D-Leu-Trp-Tyr-Pro-Gly-amide

| 44 | 4-hydroxybenzyl (Tyr) | isobutyl (Leu) | indole-CH2- (Trp) | -(CH2)3-NH-C(=NH)-NH2 (Arg) | Et | pGlu-His-Trp-Ser-Tyr-D-Leu-Trp-Arg-Pro-NHEt

| 45 | 4-hydroxybenzyl (Tyr) | isobutyl (Leu) | isobutyl (Leu) | 4-hydroxybenzyl (Tyr) | Et | pGlu-His-Trp-Ser-Tyr-D-Leu-Leu-Tyr-Pro-NHEt

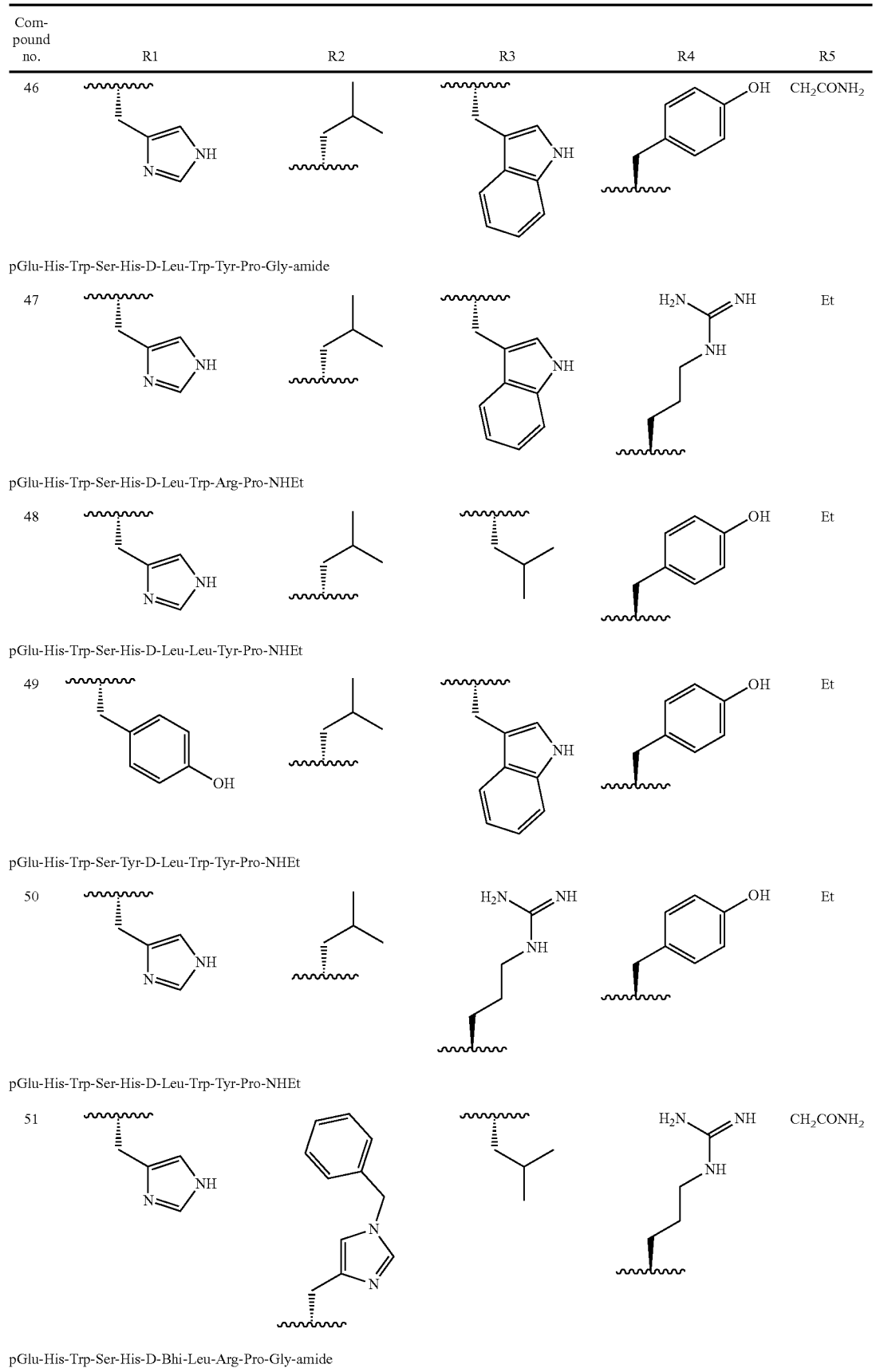

-continued

| Compound no. | R1 | R2 | R3 | R4 | R5 |
|---|---|---|---|---|---|
| 52 | 4-hydroxybenzyl (Tyr) | 1-benzyl-imidazol-4-ylmethyl (Bhi) | indol-3-ylmethyl (Trp) | 3-guanidinopropyl (Arg) | CH₂CONH₂ | pGlu-His-Trp-Ser-Tyr-D-Bhi-Trp-Arg-Pro-Gly-amide

| 53 | 4-hydroxybenzyl (Tyr) | 1-benzyl-imidazol-4-ylmethyl (Bhi) | isobutyl (Leu) | 4-hydroxybenzyl (Tyr) | CH₂CONH₂ | pGlu-His-Trp-Ser-Tyr-D-Bhi-Leu-Tyr-Pro-Gly-amide

| 54 | imidazol-4-ylmethyl (His) | 1-benzyl-imidazol-4-ylmethyl (Bhi) | indol-3-ylmethyl (Trp) | 3-guanidinopropyl (Arg) | CH₂CONH₂ | pGlu-His-Trp-Ser-His-D-Bhi-Trp-Arg-Pro-Gly-amide

| 55 | imidazol-4-ylmethyl (His) | 1-benzyl-imidazol-4-ylmethyl (Bhi) | isobutyl (Leu) | 4-hydroxybenzyl (Tyr) | CH₂CONH₂ | pGlu-His-Trp-Ser-His-D-Bhi-Leu-Try-Pro-Gly-amide

-continued
| Compound no. | R1 | R2 | R3 | R4 | R5 |
|---|---|---|---|---|---|
| 56 | 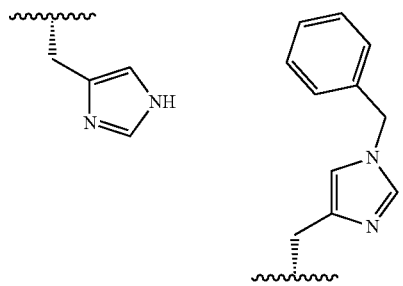 | | | | Et |
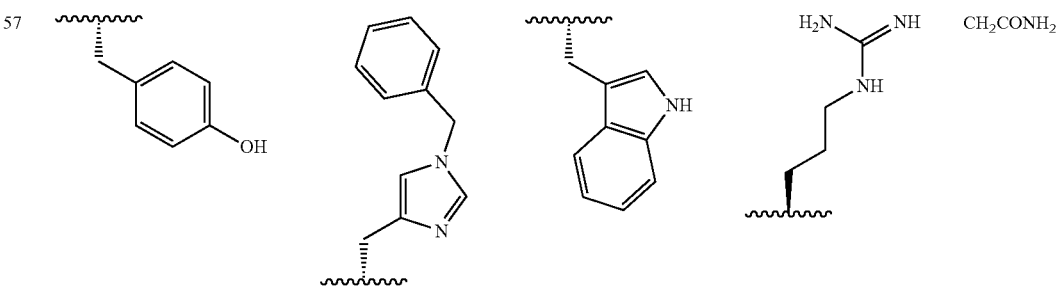
pGlu-His-Trp-Ser-His-D-Bhi-Leu-Arg-Pro-NHEt
| 57 | | | | | CH$_2$CONH$_2$ |
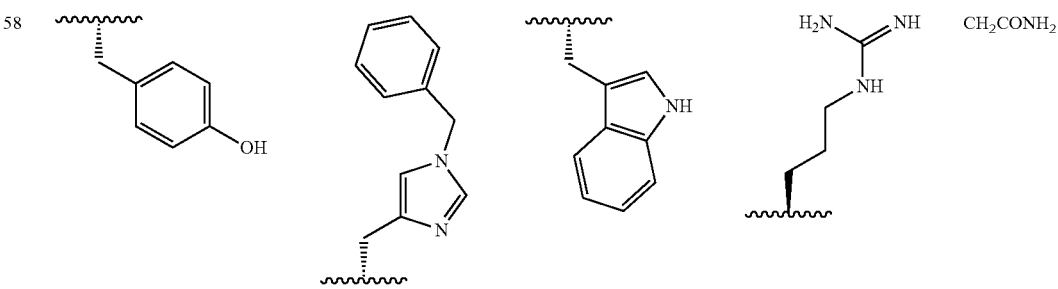
pGlu-His-Trp-Ser-Tyr-D-Bhi-Trp-Arg-Pro-Gly-amide
| 58 | | | | | CH$_2$CONH$_2$ |
pGlu-His-Trp-Ser-Tyr-D-Bhi-Trp-Arg-Pro-Gly-amide
| 59 | | | | | Et |
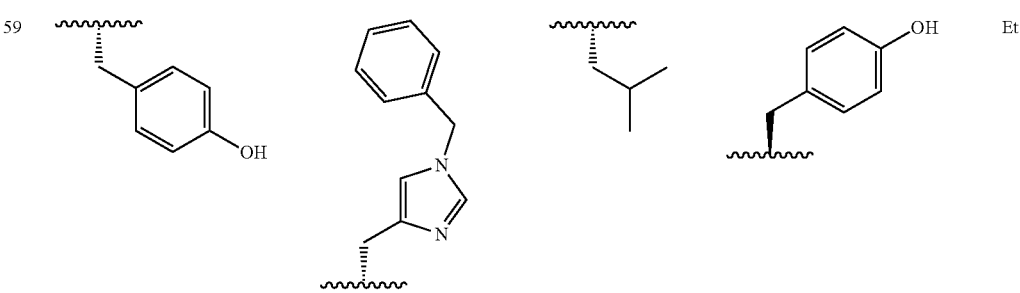
pGlu-His-Trp-Ser-Tyr-D-Bhi-Leu-Tyr-Pro-NHEt -continued
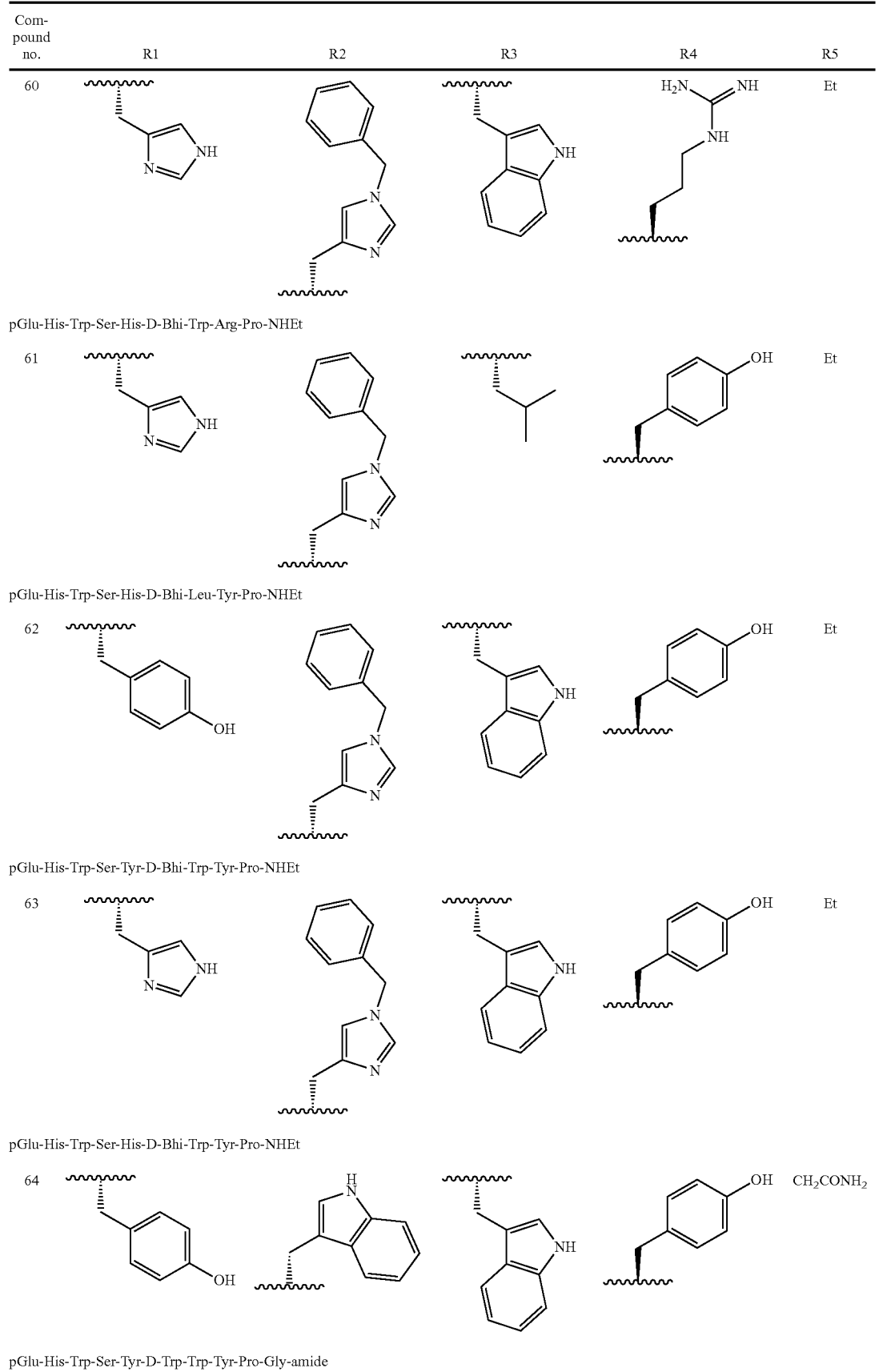
pGlu-His-Trp-Ser-His-D-Bhi-Trp-Arg-Pro-NHEt (60)
pGlu-His-Trp-Ser-His-D-Bhi-Leu-Tyr-Pro-NHEt (61)
pGlu-His-Trp-Ser-Tyr-D-Bhi-Trp-Tyr-Pro-NHEt (62)
pGlu-His-Trp-Ser-His-D-Bhi-Trp-Tyr-Pro-NHEt (63)
pGlu-His-Trp-Ser-Tyr-D-Trp-Trp-Tyr-Pro-Gly-amide (64)

| Compound no. | R1 | R2 | R3 | R4 | R5 |
|---|---|---|---|---|---|
| 65 | imidazole-CH | indole-CH (NH) | indole-CH | 4-hydroxybenzyl | CH$_2$CONH$_2$ | pGlu-His-Trp-Ser-His-D-Trp-Trp-Tyr-Pro-Gly-amide

| 66 | 4-hydroxybenzyl | indole-CH (NH) | indole-CH | guanidino-propyl | CH$_2$CONH$_2$ | pGlu-His-Trp-Ser-Tyr-D-Trp-Trp-Arg-Pro-Gly-amide

| 67 | 4-hydroxybenzyl | N-benzyl-imidazole-CH | indole-CH | guanidino-propyl | Et | pGlu-His-Trp-Ser-Tyr-D-Bhi-Trp-Arg-Pro-NHEt

| 68 | imidazole-CH | indole-CH (NH) | isobutyl | guanidino-propyl | CH$_2$CONH$_2$ | pGlu-His-Trp-Ser-His-D-Trp-Leu-Arg-Pro-Gly-amide

Of particular interest are compounds that are GnRH II analogues predominantly having i) stimulating effect on or ii) affinity for type II GnRH receptor. Thus, compounds are preferred that do not bind to or activate type I GnRH receptor resulting in an undesired therapeutic response. It is contemplated that GnRH II analogues that do bind to or activate type I GnRH receptor thereby stimulating endocrine signalling are administered together with a sex hormone to counter endocrine effects.

The present invention also provides a method for treating intracellular infections such as infections by intracellular bacteria, protozoa and fungi.

The compounds of the invention is contemplated to induce improved MHC II and MHC I antigen presentation, which make them useful in the treatment of intracellular bacterial, fungal, and protozoal infections. The present invention further provides a method for treating intracellular infection which comprises administration of an unphysiological amount of GnRH or a GnRH analog.

In Case that GnRH Analogs of the Invention Interact with Type I GnRH Receptor

GnRH analogs are known in the art. A GnRH analog is an agent that mimics the action of GnRH on the receptors of the anterior pituitary gland when administered to an animal including man. Whereas administration of a GnRH analog in a single low physiological dose or in single low physiological doses spaced in time does stimulate the receptors of the anterior pituitary gland and thus acts as a receptor agonist, the continuous administration of a GnRH analog in a high unphysiological dose per time unit will, after initial stimulation of the receptors of the anterior pituitary gland, inhibit the secretion of FSH and LH, and thus acts as a receptor antagonist.

Inhibition of FSH and LH secretion induces pharmacological castration. In this context, an unphysiological dose of a GnRH or GnRH analog is a dose resulting in an unphysiological plasma level of GnRH or GnRH, respectively, which may result in a castrating plasma level. In this context, an unphysiological plasma level of GnRH or GnRH analog is a level not comprised by range of levels of GnRH normally present or, in case of GnRH analogs, a level not comprised in regard of physiological effect by the normal physiological effect range of GnRH in a healthy person.

More particularly, an unphysiological plasma level of GnRH is a level increased, in particular increased for an extended period of time such as for more than a week or more than a month, in respect of the normal physiological plasma level of GnRH. Also, more particularly, an unphysiological plasma level of GnRH analog is an increased plasma level of GnRH analog not comprised in respect of physiological effect by the normal physiological effect range GnRH in a healthy person, in particular not for an extended period of time such as for more than a week or more than a month. Any useful form of administration of the GnRH or GnRH analog of the invention including their pharmaceutically acceptable salts is comprised by the invention, in particular intravenous, intramuscular, subcutaneous, sublingual, and nasal administration. Particular preferred are depot and slow or sustained release compositions.

If a compound of the present invention interact with type I GnRH receptor and an undesired effect may be obtained, such a compound may be administered in combination with one or more natural, semi-synthetic or synthetic sex hormones to counter the endocrine effects of GnRH II-like peptides, e.g. testosterone or oestrogen depending on the hormonal status of the patient. In an adult male person the natural, semi-synthetic or synthetic sex hormone is testosterone or an agent having a corresponding hormonal effect. In an adult female person the natural, semi-synthetic or synthetic sex hormone is oestradiol or an agent having a corresponding hormonal effect, in particular in combination with a progestogen. The latter is added to avoid the development of endometrial cancer in the female and to avoid vaginal bleedings. Hysterectomized women, however, do not benefit from the addition of progestogen.

The combined administration of one or more natural, semi-synthetic or synthetic sex hormones can be i) at the same time, i) the GnRH analog can be administered earlier than the sex hormone, or iii) the GnRH analog can be administered later than the sex hormone. Moreover, and dependent on the administration form used, the GnRH analog and/or the hormone may be administered more than one time such as eg in case of administration of the sex hormone via nasal spray, where administration typically is one or more times a day during one or more weeks.

The combined administration may extend, for instance, for over one or more periods interrupted by administration-free periods, or the administration can be continuous. A preferred administration period is from one to two weeks, in particular from 10 to 14 days. If a compound of the present invention has an endocrine effect by activating GnRH I it is preferred that the administration of said compound substantially overlaps the period of administration of one or more natural, semi-synthetic or synthetic sex hormones, such as by more than 50 percent, preferably by more than 85 percent, even more preferred by more than 90 or 95 percent. The combined administration allows to protect the person from serious endocrine side effects, such as decreased libido, hot flushes, increased perspiration, and increased heart rate.

In an adult male person the natural, semi-synthetic or synthetic sex hormone administered to counter the endocrine effect of a compound of the invention is testosterone or an agent having a corresponding hormonal effect, in particular synthetic or semisynthetic agents that mimic the hormonal effects of testosterone. Preferred agents comprise methyltestosterone and stanozolol. In an adult female person the natural, semi-synthetic or synthetic sex hormone administered to counter the endocrine effect of a compound of the invention is an oestrogen such as oestradiol or a semisynthetic ester of oestradiol or another synthetic or semi-synthetic oestrogen analog. Preferred oestrogen analogs comprise conjugated oestrogens, ethynylestradiol, and mestranol, as well as non-steroidal oestrogens such as dinestrol and diethylstilbestrol. In a female said oestrogen or oestrogen analog administration is in one aspect preferably combined in combination with administration of a progestogen, in particular progesterone, a progesterone derivative or analog, such as hydroxyprogesterone caproate, medroxyprogesterone acetate, noethisterone acetate, megestrol acetate, medrogestone and norgestrel. The combined administration preferably overlaps by more than 50 percent, preferably by more than 85 percent, even more preferred by more than 90 or 95 percent. It is preferred that the progestogen to be administered in combination with the oestrogen, the semisynthetic ester of oestradiol or estriol or the synthetic or semisynthetic oestrogen analog continuously or over periods of from about 10 to 14 days in intervals from about one to three months.

If necessary, a natural, semisynthetic, or synthetic sex hormone is administered in combination with a type I GnRH receptor-activating compound of the invention, and optionally with a pharmaceutically acceptable carrier.

General Chemistry Methods

The skilled person will recognise that the compounds of the invention may be prepared, in known manner, in a variety of ways. The routes below are merely illustrative of some methods that can be employed for the synthesis of compounds of formula (I).

In general, synthetic methods for preparing compounds of the invention can be divided into two methods: liquid phase synthesis and solid phase synthesis. Liquid phase peptide synthesis involves reagents reacting together in the solution phase. Disadvantages of this method include difficulty in separating and purification of the products. Solid phase peptide synthesis is more common and has numerous advantages including convenient isolation and purification and applicability to automation (Bodanszky et al, In Peptide Synthesis, John Wiley & Sons, 1976). Many peptide synthetic resins have been developed to allow synthesis of various peptides. These include chloromethyl and 2-chlorotityl polystyrene resins. Examples of patents disclosing methods for synthesis of short peptides include U.S. Pat. No. 5,602,231, EP0518655 and U.S. Pat. No. 6,879,289.

When a compound of the invention is prepared with a C-terminal secondary amide, as in e.g. buserelin, then one method of preparing the compounds is as follows and depicted in scheme I below. The peptide can be assembled on a solid support, typically 2-chlorotrityl polystyrene resin is used, but others will be apparent to one skilled in the art. The first amino acid is loaded and then deprotected to reveal a reactive amine group that is then used to couple onto the next amino acid. This in turn can be deprotected and coupled. After multiple rounds of extension, the desired peptide sequence is obtained. The peptide is then cleaved from the resin by the action of TFA or similar reagents. Note that when a tert-butyl side chain is required in the final compound it is important to keep the reaction time low enough such that this does not cleave entirely. Some tert-butyl will cleave but this can be removed in purification.

Finally, the secondary amide is prepared by coupling the deprotected peptide at the C-terminus with a selected primary amine. Coupling reactions typically utilise HBTU and DIPEA, though one skilled in the art will be able to identify other activators and bases that can be used in combination to effect the amide bond formation.

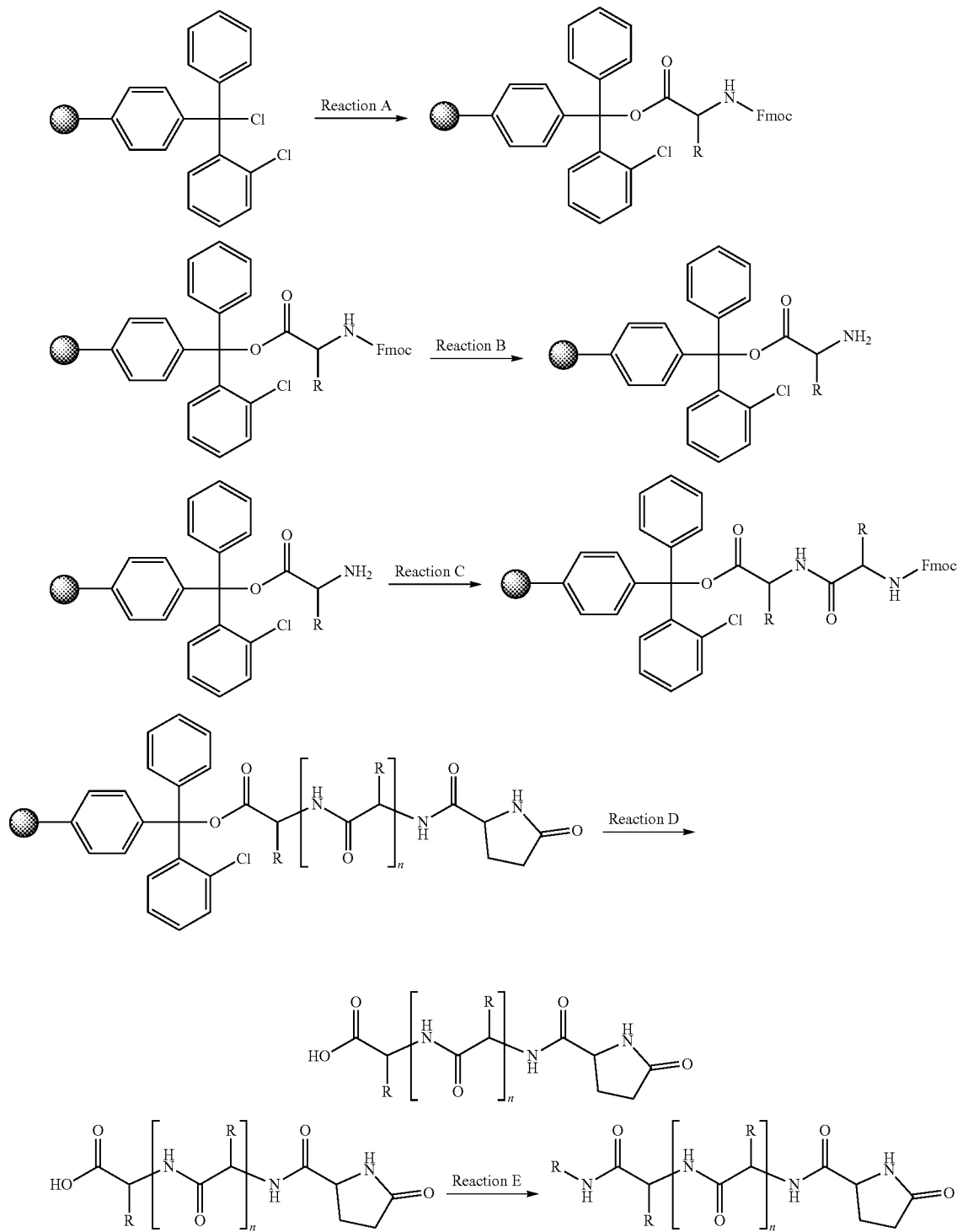

Scheme I

When a compound of the invention is prepared with a C-terminal primary amide, as in e.g. triptorelin, then one method of preparing the compounds is as follows and depicted in scheme II below. The peptide can be assembled on a solid support, typically Ramage resin is used, but others will be apparent to one skilled in the art. The first amino acid is loaded and then deprotected to reveal a reactive amine group that is then used to couple onto the next amino acid. This in turn can be deprotected and coupled. After multiple rounds of extension, the desired peptide sequence is obtained. The peptide is then cleaved from the resin by the action of TFA or similar reagents. Coupling reactions typically utilise HBTU and DIPEA, though one skilled in the art will be able to identify other activators and bases that can be used in combination to effect the amide bond formation.

Scheme II

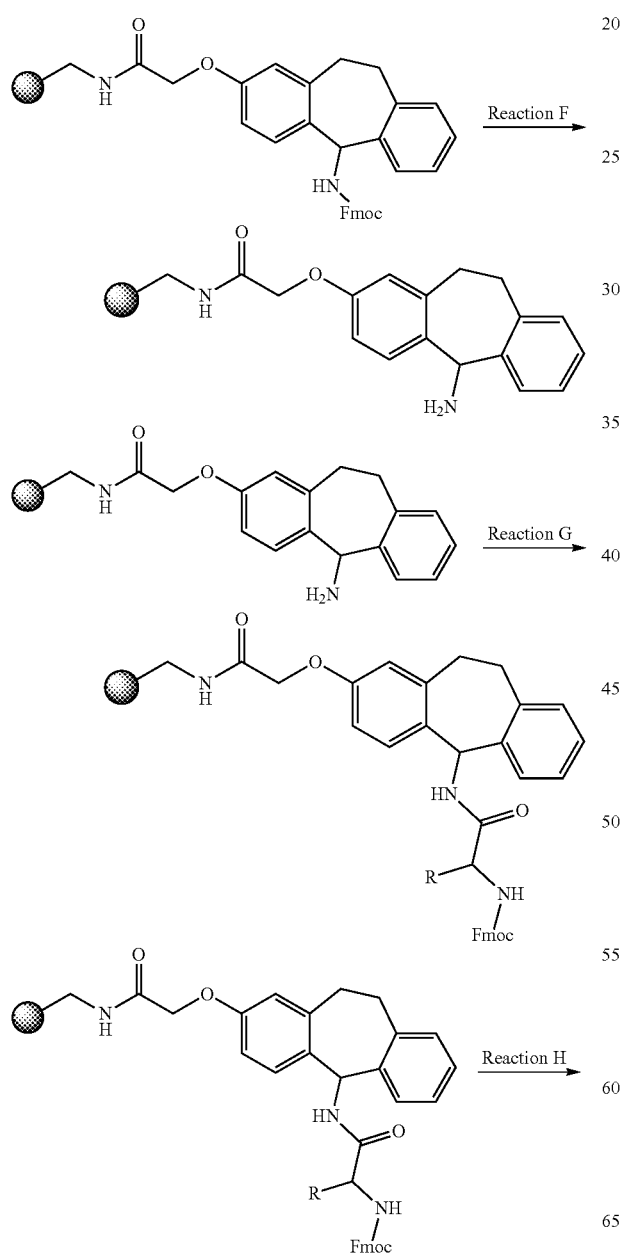

-continued

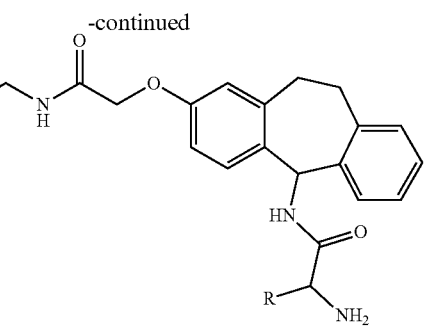

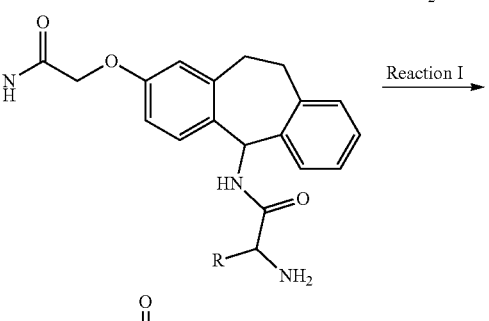

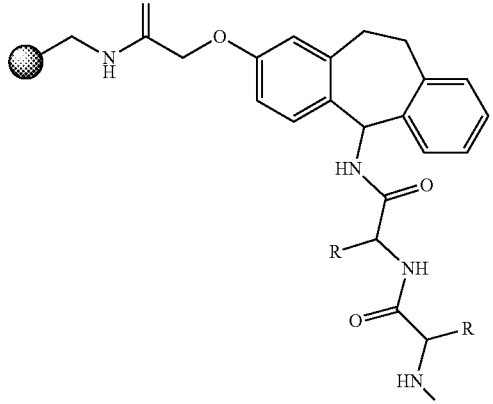

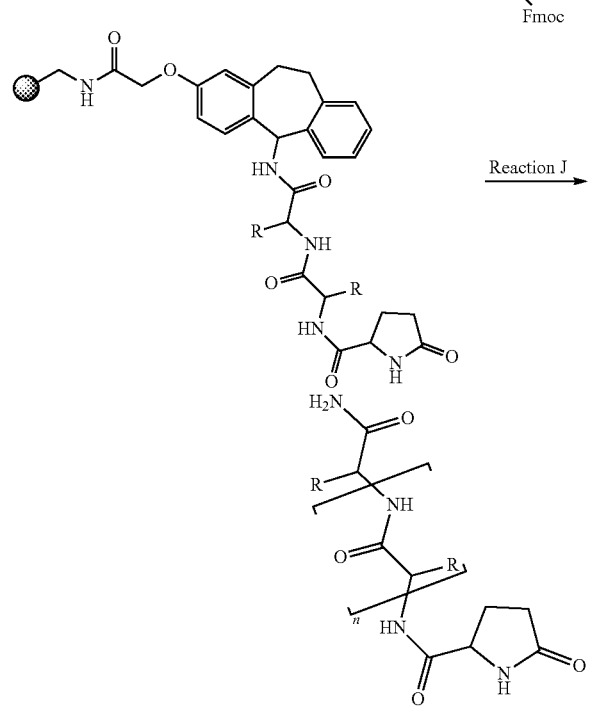

Compounds of formula (I) may be made by combining the methods describe above and by other methods known to one skilled in the art.

General Use of the Compounds of the Invention

Compounds as described herein can be used in medicine, medical research or in the manufacture of a composition for such use. Moreover, the invention also relates to the compounds P1-P21 as described herein for use in medicine, medical research or in the manufacture of a composition for such use. Accordingly, when in the following the term "compounds of the invention" is used in connection with medical use or pharmaceutical composition, the term is intended also to include compounds P1-P21 provided that these compounds have not been known for such a use.

In addition, the compounds are contemplated to show improved properties for treatment of intracellular infection and related diseases, including reduced binding to type I GnRH receptor as compared to type II GnRH receptor.

The compounds of the invention are contemplated to be of use in the treatment of intracellular bacterial, fungal, and protozoal infections, such as *Mycobacterium tuberculosis*, Mycobacteria causing atypical disease, *Mycobacterium avium* and *M. intracellulare* (also known as *Mycobacterium avium-intracellulare* complex, or MAC), *M. kansasii, M. marinum, M. fortuitum, M. gordinae, Mycoplasma pneumoniae, M. genitalium, M. hominis, Ureaplasma urealyticum, U. parvum, Chlamydophila pneumoniae*, and *Salmonella typhimurium*, and in the treatment of intracellular protozoal infections, such as *Toxoplasma gondii, Plasmodium falciparum, P. vivax, Trypanosoma cruzi, Cryptosporidium*, and *Leishmania*, and intracellular fungal infections such as *Histoplasma capsulatum, Cryptococcus neoformans*, and *Encephalitozoon cuniculi* when these infections occur alone or in association with viral agents or viral diseases, or in association with other causes of primary or secondary immunodeficiency. Causes of primary immunodeficiency include inherited genetic deficiencies and somatic mutations, whereas secondary immunodeficiency may be caused by viral infections such as those described above, or by inheritable or non-inheritable conditions such as Diabetes mellitus, or malnutrition, or by agents such as immunodepressants, drug abuse, or other environmental factors.

Moreover, the compounds of the invention disclosed herein may be used as a co-treatment to of viral diseases, disorders, conditions, and symptoms, such as in treating patients infected with viral agents or with viral diseases such as HIV, Adenovirus, Alphavirus, Arbovirus, Borna Disease, Bunyavirus, Calicivirus, Condyloma Acuminata, Coronavirus, Coxsackievirus, Cytomegalovirus, Dengue fever virus, Contageous Ecthyma, Epstein-Barr virus, Erythema Infectiosum, Hantavirus, Viral Hemorrhagic Fever, Viral Hepatitis, Herpes Simplex Virus, Herpes Zoster virus, Infectious Mononucleosis, Influenza, Lassa Fever virus, Measles, Mumps, Molluscum Contagiosum, Paramyxovirus, Phlebotomus fever, Polyoma-virus, Rift Valley Fever, Rubella, Slow Disease Virus, Smallpox, Subacute Sclerosing Panencephalitis, Tumor Virus Infections, West Nile Virus, Yellow Fever Virus, Rabies Virus and Respiratory Syncitial Virus.

Moreover, the compounds are contemplated to be suitable for use in the treatment or co-treatment of cancer. In particular, Adrenal Cancer, Anal Cancer, Bile Duct Cancer, Bladder Cancer, Bone Cancer, Brain/CNS Tumors, Breast Cancer, Castleman Disease, Cervical Cancer, Colon/Rectum Cancer, Endometrial Cancer, Esophagus Cancer, Eye Cancer, Gallbladder Cancer, Gastrointestinal Carcinoid Tumors, Gastrointestinal Stromal Tumor (GIST), Gestational Trophoblastic Disease, Hodgkin Disease, Kaposi Sarcoma, Kidney Cancer, Laryngeal and Hypopharyngeal Cancer, Acute Myeloid Leukemia, Chronic Lymphocytic Leukemia, Acute Lymphocytic Leukemia, Chronic Myeloid Leukemia, Chronic Myelomonocytic Leukemia, Liver Cancer, Non-Small Cell Lung Cancer, Small Cell Lung Cancer, Lung Carcinoid Tumor, Lymphoma, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Oral Cavity and Oropharyngeal Cancer, Osteosarcoma, Ovarian Cancer, Pancreatic Cancer, Penile Cancer, Pituitary Tumors, Prostate Cancer, Retinoblastoma, Rhabdomyosarcoma, Salivary Gland Cancer, Basal and Squamous Cell Skin Cancer, Melanoma, Merkel Cell Skin Cancer, Small Intestine Cancer, Stomach Cancer, Testicular Cancer, Thymus Cancer, Thyroid Cancer, Uterine Sarcoma, Vaginal Cancer, Vulvar Cancer, Waldenstrom Macroglobulinemia, Wilms Tumor.

Thus the advantageous properties of the compound of the invention may include one or more of the following:
Improved binding to type II GnRH receptor as compared to type I GnRH receptor
Improved MHC class I stimulation
improved MHC class II stimulation
Improved immunomodulation
Improved activation of antigen presenting cells
Improved T-cell response
Improved antiviral activity
Improved anticancer activity
Improved MHC II antigen presentation
Improved MHC I antigen presentation Pharmaceutical Compositions Comprising a Compound of the Invention The present invention also provides a pharmaceutical composition comprising the compound of the invention together with one or more pharmaceutically acceptable diluents or carriers. The present chapter is primarily directed to formulation of the novel GnRH analogs. In those cases where the novel compounds have an effect on type I GnRH receptor, which is unwanted and causes castration or similar effects, compositions containing sex hormones are known in the art and may be co-administered.

The compounds of the invention or a formulation thereof may be administered by any conventional route for example but without limitation it may be administered parenterally, orally, topically or via a mucosa (including buccal, sublingual, transdermal, vaginal, rectal, nasal, ocular etc.), via a medical device (e.g. a stent), by inhalation. The treatment may consist of a single administration or a plurality of administrations over a period of time.

The treatment may be by administration once daily, twice daily, three times daily, four times daily etc. dependent on the specific disease to be treated and the weight and age of the patient to be treated. The treatment may also be by continuous administration such as e.g. administration intravenous by infusion via a drop.

Whilst it is possible for the compound of the invention to be administered as such, it is preferable to present it as a pharmaceutical formulation, together with one or more acceptable carriers. The carrier(s) must be "acceptable" in the sense of being compatible with the compound of the invention and not deleterious to the recipients thereof. Examples of suitable carriers are described in more detail below.

The formulations may conveniently be presented in a suitable dosage form including a unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

The compound of the invention will normally be administered by any conventional administration route normally by the oral or any parenteral route, in the form of a pharmaceutical formulation comprising the active ingredient, optionally in the form of a nontoxic organic, or inorganic, acid, or base, addition salt, in a pharmaceutically acceptable dosage form. Depending upon the disorder and patient to be treated, as well as the route of administration, the compositions may be administered at varying doses and/or frequencies.

The pharmaceutical compositions must be stable under the conditions of manufacture and storage; thus, if necessary should be preserved against the contaminating action of microorganisms such as bacteria and fungi. In case of liquid formulations such as solutions, dispersion, emulsions and suspensions, the carrier can be a solvent or dispersion medium containing, for example, water, ethanol, polyol (e.g. glycerol, propylene glycol and liquid polyethylene glycol), vegetable oils, and suitable mixtures thereof.

For example, the compound of the invention may be administered orally, buccally or sublingually in the form of tablets, capsules, films, ovules, elixirs, solutions, emulsions or suspensions, which may contain flavouring or colouring agents.

Formulations in accordance with the present invention suitable for oral administration may be presented as discrete units such as capsules, cachets or tablets, each containing a predetermined amount of the active ingredient; as multiple units e.g. in the form of a tablet or capsule: as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Solutions or suspensions of the compound of the invention suitable for oral administration may also contain one or more solvents including water, alcohol, polyol etc. as well as one or more excipients such as pH-adjusting agent, stabilizing agents, surfactants, solubilizers, dispersing agents, preservatives, flavors etc. Specific examples include e.g. N,N-dimethylacetamide, dispersants e.g. polysorbate 80, surfactants, and solubilisers, e.g. polyethylene glycol, Phosal 50 PG (which consists of phosphatidylcholine, soya-fatty acids, ethanol, mono/diglycerides, propylene glycol and ascorbyl palmitate). The formulations according to present invention may also be in the form of emulsions, wherein a compound according to Formula (I) may be present in an emulsion such as an oil-in-water emulsion or a water-in-oil emulsion. The oil may be a natural or synthetic oil or any oil-like substance such as e.g. soy bean oil or safflower oil or combinations thereof.

Tablets may contain excipients such as microcrystalline cellulose, lactose (e.g. lactose monohydrate or lactose anyhydrous), sodium citrate, calcium carbonate, dibasic calcium phosphate and glycine, butylated hydroxytoluene (E321), crospovidone, hypromellose, disintegrants such as starch (preferably corn, potato or tapioca starch), sodium starch glycollate, croscarmellose sodium, and certain complex silicates, and granulation binders such as polyvinylpyrrolidone, hydroxypropylmethylcellulose (HPMC), hydroxy-propylcellulose (HPC), macrogol 8000, sucrose, gelatin and acacia. Additionally, lubricating agents such as magnesium stearate, stearic acid, glyceryl behenate and talc may be included.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, crosslinked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollient in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base.

Alternatively, the active agent may be formulated in a cream with an oil-in-water cream base or a water-in-oil base.

For parenteral administration, fluid unit dosage forms are prepared utilizing the active ingredient and a sterile vehicle, for example but without limitation water, alcohols, polyols, glycerine and vegetable oils, water being preferred. The active ingredient, depending on the vehicle and concentration used, can be either colloidal, suspended or dissolved in the vehicle. In preparing solutions the active ingredient can be dissolved in water for injection and filter sterilised before filling into a suitable vial or ampoule and sealing.

Advantageously, agents such as local anaesthetics, preservatives and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability.

Parenteral suspensions are prepared in substantially the same manner as solutions, except that the active ingredient is suspended in the vehicle instead of being dissolved and sterilization cannot be accomplished by filtration. The active ingredient can be sterilised by exposure to ethylene oxide before suspending in the sterile vehicle. Advantageously, a surfactant or wetting agent is included in the composition to facilitate uniform distribution of the active ingredient.

It should be understood that in addition to the ingredients particularly mentioned above the formulations of this invention may include other agents conventional in the art having regard to the type of formulation in question, for example those suitable for oral administration may include flavouring agents. A person skilled in the art will know how to choose a suitable formulation and how to prepare it (see eg Remington's Pharmaceutical Sciences 18 Ed. or later). A person skilled in the art will also know how to choose a suitable administration route and dosage.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

A pharmaceutical composition may also be a two-part composition, where one part contains the GnRH analogue and the other part contains the sex hormone. The two parts may be combined eg as a two-layer tablet or they may be present eg as pellets in a capsule. Known compositions containing a GnRH analogue and known compositions containing a sex hormone may also be used in a method of the invention.

All % values mentioned herein are % w/w unless the context requires otherwise.

Sequence List

The sequence list is prepared according to the WIPO standard ST.25. In the sequence list, the unnatural amino acids of compounds 1-63 and P1-P21 are represented as the corresponding natural amino acid in the following way:

| Unnatural amino acid | Corresponding natural amino acid |
|---|---|
| pGlu, pyroglutamate | L-Glutamate, Glu |
| 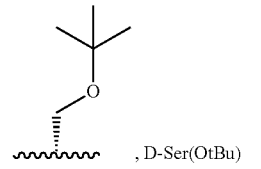, D-Ser(OtBu) | L-Serine, Ser |
| 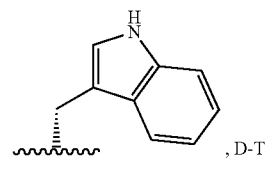, D-Trp | L-Tryptophan, Trp |
| 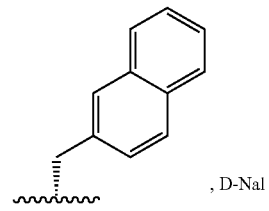, D-Nal | L-Phenylalanine, Phe |
| 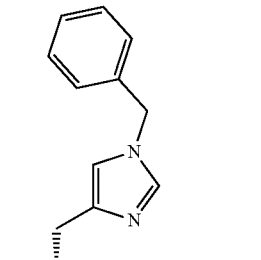, D-Bhi | L-Histidine, His |
| 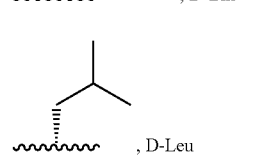, D-Leu | L-Leucine, Leu |
| Pro-Et | L-Proline, Pro |
| Pro-NHCONH$_2$ | L-Proline, Pro |
| Gly-NH$_2$ | Gly |

In the sequence list, entries 1-63 correspond to compounds 1-63, and entries 64-78 correspond to compounds P1-P15. Entries 79 and 80 correspond to wild-type GnRH I and GnRH II. Entries 81-84 correspond to primers. Entries 85-89 correspond to compounds 64-68. Entries 90-95 correspond to compounds P16-P21. However, the sequences SEQ ID Nos: 1-78 and 85-89 as they are stated in the sequence list, i.e. without above-described unnatural amino acids, are not claimed, but are included only to comply with the requirements of R. 30(1) of the EPC.

Repetition of Free Text from Sequence Listing

For compliance with paragraph 36 of WIPO Standard ST.25, the free text included under numeric identifier <223> of the sequence listing is hereby repeated in the main part of the description:

| SEQ ID NO | Free text included in <223> |
|---|---|
| 1-78 | Man-made analogue of GnRH II |
| 79 | GnRH I |
| 80 | GnRH II |
| 81 | Type I GnRH Receptor forward primer |
| 82 | Type I GnRH Receptor reverse primer |
| 83 | Type II GnRH Receptor forward primer |
| 84 | Type II GnRH Receptor reverse primer |
| 85-95 | Man-made analogue of GnRH II |

Definitions

The articles "a" and "an" are used herein to refer to one or to more than one (i.e. at least one) of the grammatical objects of the article. By way of example "an analogue" means one analogue or more than one analogue.

As used herein the terms "immunorhelins" and "compound(s) of the invention" are used interchangeably and refer to compounds of formula (I).

The pharmaceutically acceptable salts of the compound of the invention include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

LEGENDS TO FIGURES

FIG. 1: Expression of MHC class I after stimulation of T cells with increasing concentrations of GnRH II. PBMCs from a healthy donor was stimulated with GnRH II and IL-2 for 72 hours. Data points represent mean fluorescent intensity of MCH class I expression on CD4$^+$ T cells (blue triangles) or CD8$^+$ T cells (black squares) measured with flow cytometry.

FIG. 2: Expression of MHC class I after stimulation of T cells with increasing concentrations of GnRH I analogue (red) and GnRH II. (black). PBMCs from a healthy donor was stimulated with GnRH I analogoue or with GnRH II and IL-2 for 72 hours. Data points represent mean fluorescent intensity of MCH class I expression on CD4$^+$ T cells (A) or CD8$^+$ T cells (B) measured with flow cytometry.

Figure 3:
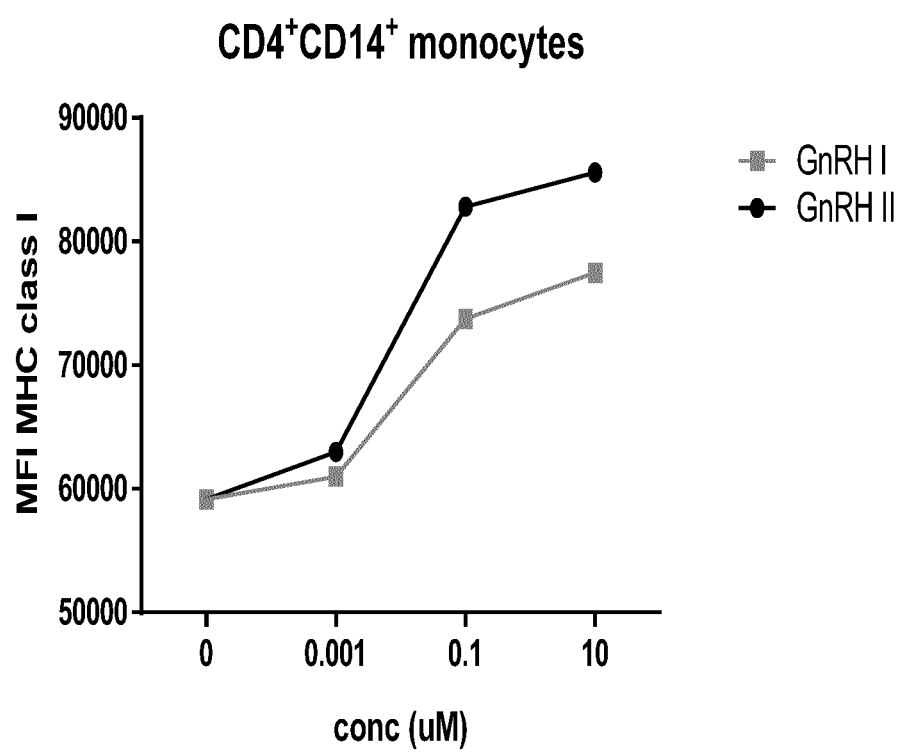

FIG. 3: Expression of MHC class I after stimulation of CD4$^+$CD14$^+$ monocytes with increasing concentrations of GnRH I analogue (red) and GnRH II (black). CD14$^+$ monocytes PBMCs from a healthy donor was stimulated with GnRH I analogue or with GnRH II and IL-2 for 72 hours. Data points represent mean fluorescent intensity of MCH class I expression on CD4$^+$CD14$^+$ monocytes measured with flow cytometry.

FIG. 4: GnRH receptor expression in human T cells analysed with quantitative real-time PCR. The bars represent ratios of GnRHR I or GnRHR II mRNA normalized to RNA polymerase II expression in sorted naive T cells (white bars) or memory T cells (gray bars). MCF-7 breast cancer cell line (black bar) was used as a positive control.

Figure 5:
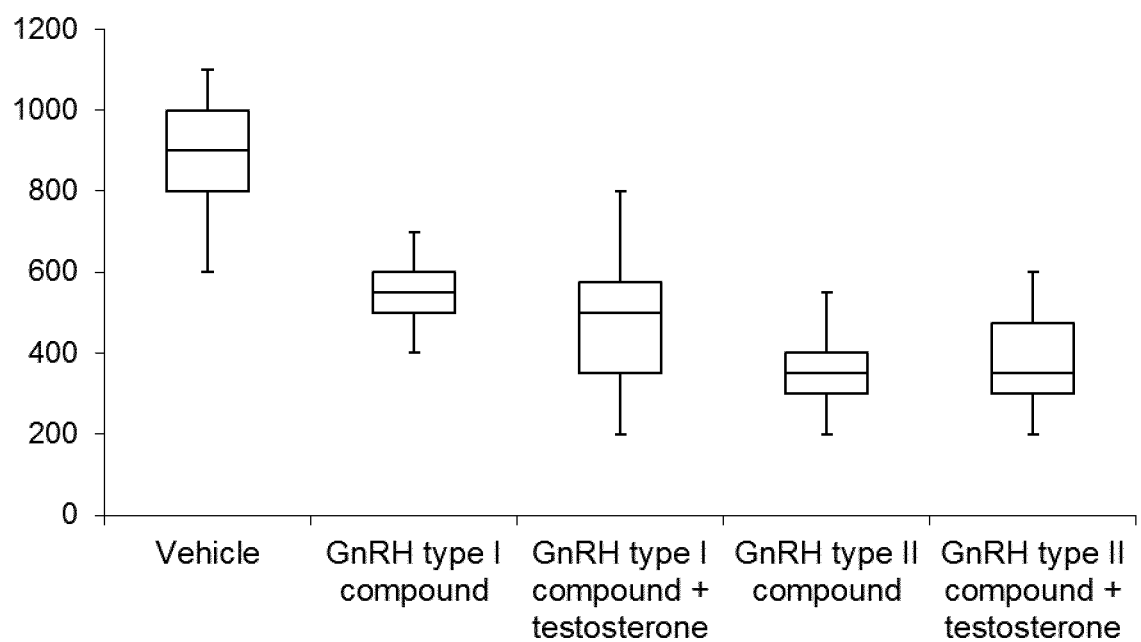

FIG. 5: Expected data: Number of mycobacteria in the lungs of infected mice are suppressed by compounds of the present invention in the presence or absence of testosterone. Colony Forming Units (CFU) are assessed by growing lysates of lung tissue from infected mice on bacterial plates and counting colonies.

EXPERIMENTAL

General Biology Methods

The preferential effect of the compounds of the invention on GnRH receptors may be tested using one or more of the methods described below:

I. Expression of GnRH Receptors on T Cells

Human naive and memory T cells were labeled with fluorescent surface marker antibodies CD45RA, CD45RO and CD4 and sorted with flow cytometry. Total RNA was extracted with Rnaeasy kit (Qiagen) and reversed transcribed with iScript select cDNA synthesis kit (Biorad). The template cDNA was amplified with SYBR Green (Applied Biosystem) and run on CFX96 PCR (Biorad). Ratios of Type I GnRH Receptor and Type II GnRH Receptor mRNA were normalized to RNA polymerase II expression in sorted naive T cells or memory T cells. The MCF-7 breast cancer cell line was used as a positive control.

Primer Sequences:

```
Type I GnRH Receptor
fwd
5'-tgc ctc ttc atc atc cct ct-3' rev
5'-gca aat gca acc gtc att tt-3'

Type II GnRH Receptor
fwd
5'-act gtt caa tgg ctg gct gt-3' rev
5'-gcc ccc aga agt ttc ctt ac-3'
```

I. GnRH I Vs GnRH II Assay

Compounds were tested on cells made to express Type I or Type II GnRH Receptors by transfection. The cells were exposed to labelled GnRH compound, washed and then assessed by measuring the label on the cells. The label was either measured directly (radioactive isotope label or fluorescent label) or indirectly (biotin labelled peptide).

Signalling induced by the GnRH compounds was measured in the cell lines expressing Type I GnRH and Type II GnRH Receptors respectively. GnRH compounds were investigated for their respective affinity to type I GnRH and type II GnRH receptors using competition assays. Calcium flux was measured using cells labelled with Fluo-4-Direct either using a flow cytometer or by live cell imaging microscopy, in order to evaluate their potency establishing ED50 values. Signalling was also studied by western blotting using antibodies to p-ERK or p-JNK.

To assess the effects of cellular activation on the production of LH and FSH and compare it with stimulation of immune related functions, the effects of the compounds were studied on pituitary cells and immune cells expressing either Type II GnRH or Type I GnRH Receptors.

II. Expression of Cell Specific Surface Markers and MHC Class II and MHC Class I Human peripheral blood mononuclear cells (PBMCs) were purified from healthy donors with Ficoll-Hypaque density centrifugation. Cells were cultured in RPMI-1640 medium (Invitrogen) supplemented with 10% fetal bovine serum, 100 µg/mL ampicilin and 100 µg/mL streptomycin for 24-72 hours in 37° C., 5% $CO_2$. Cells were stimulated with a compound according to the invention and analysed for expression of cell specific surface markers and MHC class II (monoclonal antibodies from BD Pharmingen) with flow cytomtery.

To test a set of compounds according to the invention for their immunomodulatory properties in an in vitro assay and evaluate their ability to induce MHC class II expression on monocytes. First when a known GnRH analogue was used in a co-culture to stimulate monocytes. A small increase in MHC class expression from background of in MFI may be seen. In contrast, when a compound according to the invention is used we may detect a larger expression of cell surface expression of MHC class II. If this is the observation, we may have identified a compound with an effect on MHC class II expression, allowing increased turnover and presentation of MHC class II and class I peptides from the endosomal and lysosomal pathway. The findings will enhance the presentation of peptides derived from intracellular pathogens and promote CD4[+] helper T as well as CD8+ T cells activation, expansion and induce sterilizing immunity.

Materials

Unless otherwise indicated, all reagents used in the examples below are obtained from commercial sources.

Theoretical Example of the Compounds of the Invention on Intracellular Bacteria

Material and Methods

Male mice are infected with *Mycobacterium tuberculosis* by inhalation of an aerosol containing the bacteria. The infecting dose is between 100 and 1000 bacteria per mouse. The GnRHII or GnRHI related compound (alone or together with testosterone) or vehicle is administered by an appropriate route in an appropriate dose for 1-2 weeks following infection with the bacteria either. The mice are sacrificed and lungs removed and homogenized and plated on bacteria dishes containing medium that supports the growth of *Mycobacterium tuberculosis*. After 3-4 weeks incubation, in a heated cabinet at 37 degrees C., the amount of bacteria in the lungs of the mice are quantified by counting bacterial colonies on the plate.

Expected Results

Expected results of this experiments is that the amount of *Mycobacterium tuberculosis* bacteria in the lungs of mice are reduced in mice treated with GnRH compounds compared with control vehicle treated mice. We also expect GnRHII related compounds to be superior to GnRHI related compounds in this respect. We do not expect co-administration of testosterone will have any effect on the degree of effect of the GnRH compounds.

Measurement of Castractive Effects and Compensation Thereof

Castration induced by the compounds of the invention, as well as any compensation thereof can be determined by measurement of the circulating levels of the relevant sex hormones. How to carry out such measurements is known to the person skilled in the art.

General Synthesis Method

Method A

-continued

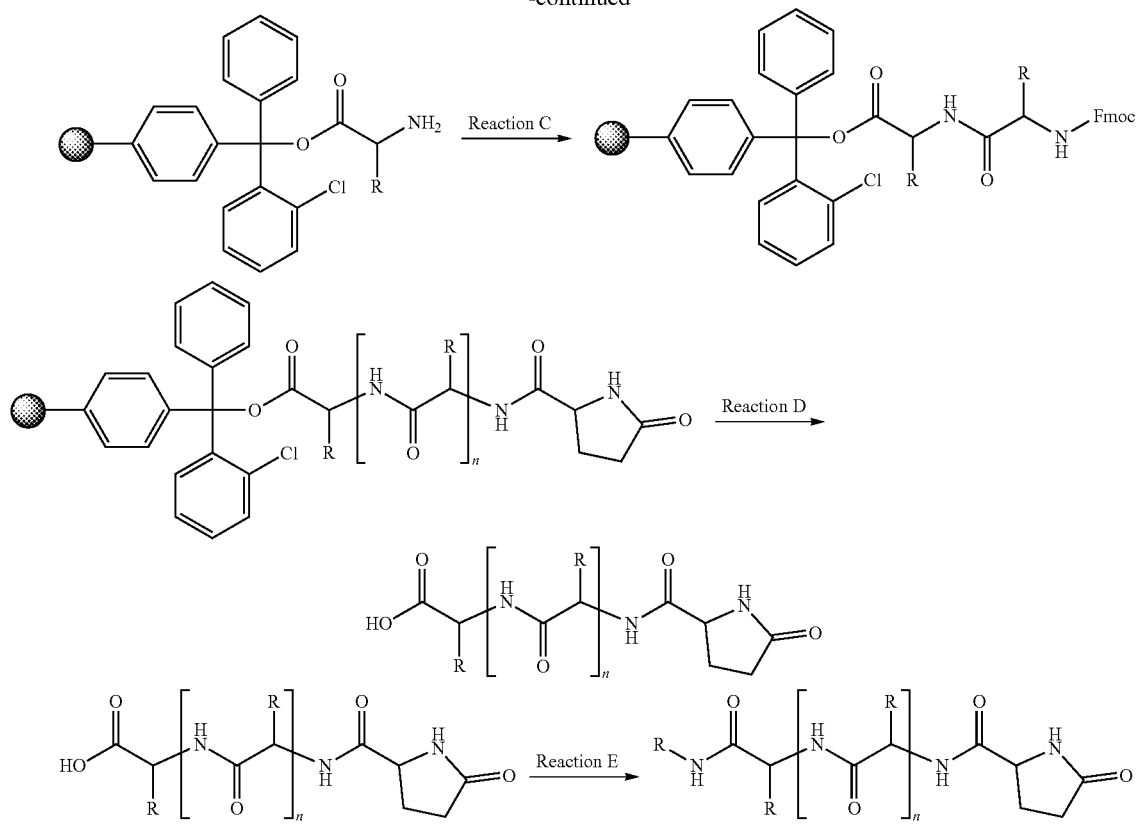

Peptides were prepared using standard Fmoc solid-phase synthesis as per the diagram above. Protected amino acids (Fmoc and tBu or Trt if necessary) were used, and synthesis was performed on 2-chlorotrityl polystyrene resin. Reactions are carried out in the order A, B, C followed by multiple iterations of B and C to build up the desired peptide. When the final amino acid (pyroglutamate—note, reaction C is used to do this, though the amino acid is not Fmoc protected) have been added the final two reactions—D and E—take place in that order to generate a compound of the invention.

Reaction A:

The resin was suspended in dichloromethane (10-20 volume equivalents compared to the resin) and stirred at room temperature. Fmoc protected amino acid (2 equivalents) was added to 1 equivalent of resin in the presence of diisopropylethylamine (6 equivalents). The reaction was stirred for 0.5 to 1 hour at room temperature. The resin was collected by filtration and washed 6 times with DMF and then used directly in the next step.

Reaction B:

The Fmoc protecting group was removed by the treatment of piperidine (20%) in dimethylformamide (5-10 volume equivalents compared to the resin) at room temperature. The reaction was stirred for up to 1 hour and the resin collected b filtration and then the resin was washed 6 times with DMF and used directly in the next step.

Reaction C:

Fmoc-protected amino acid (4 equivalents) was dissolved in DMF and DIPEA (2 equivalents) added. After stirring at room temperature for one minute these were added to the resin supported amino acid (1 equivalent) from Reaction B was treated with HBTU (1 equivalent) added. The reaction was stirred for up to one hour and before the resin was collected by filtration and washed 6 times with DMF and used directly in the next step. The next step was either reaction B or reaction D depending on the target sequence.

Reaction D:

The protected peptide was cleaved from the resin by treatment with 3-5% trifluoroacetic acid in dichloromethane. The resin was removed by filtration and the peptide accrued by precipitation with ice cold diethyl ether and collection by centrifugation. The solid was washed in further diethyl ether and then dried under vacuum before being used in the next step.

Reaction E:

The C-terminal amide was formed by dissolving the peptide from Reaction D (1 equivalent) in DMF, monoalkylamine (20-50 equivalents) and HBTU (2-3 equivalents) were added and the reaction stirred at room temperature for up to 3 hours. The reaction was diluted with water and the crude peptide was then purified as detailed below.

Method B

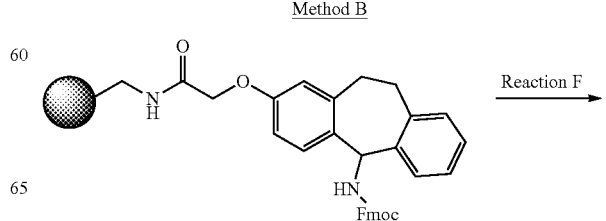

Reaction F

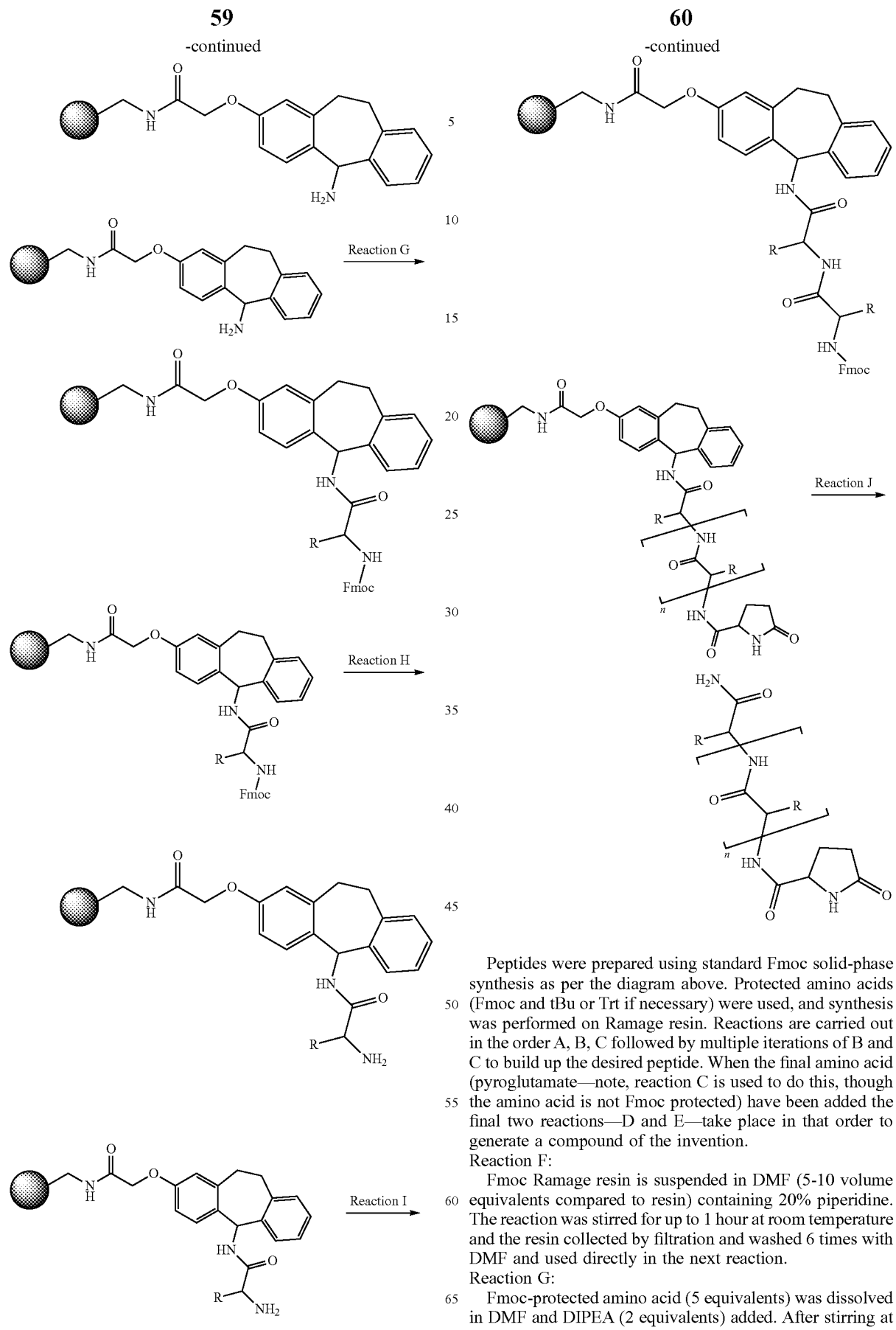

Peptides were prepared using standard Fmoc solid-phase synthesis as per the diagram above. Protected amino acids (Fmoc and tBu or Trt if necessary) were used, and synthesis was performed on Ramage resin. Reactions are carried out in the order A, B, C followed by multiple iterations of B and C to build up the desired peptide. When the final amino acid (pyroglutamate—note, reaction C is used to do this, though the amino acid is not Fmoc protected) have been added the final two reactions—D and E—take place in that order to generate a compound of the invention.

Reaction F:

Fmoc Ramage resin is suspended in DMF (5-10 volume equivalents compared to resin) containing 20% piperidine. The reaction was stirred for up to 1 hour at room temperature and the resin collected by filtration and washed 6 times with DMF and used directly in the next reaction.

Reaction G:

Fmoc-protected amino acid (5 equivalents) was dissolved in DMF and DIPEA (2 equivalents) added. After stirring at room temperature for one minute these were added to the resin supported amino acid (1 equivalent) from Reaction F was treated with HBTU (1 equivalent) added. The reaction was stirred for up to one hour and before the resin was collected by filtration and washed 6 times with DMF and used directly in the next step.

Reaction H:

The Fmoc protecting group was removed by the treatment of piperidine (20%) in dimethylformamide (5-10 volume equivalents compared to the resin) at room temperature. The reaction was stirred for up to 1 hour and the resin collected b filtration and then the resin was washed 6 times with DMF and used directly in the next step.

Reaction I:

Fmoc-protected amino acid (4 equivalents) was dissolved in DMF and DIPEA (2 equivalents) added. After stirring at room temperature for one minute these were added to the resin supported amino acid (1 equivalent) from Reaction H was treated with HBTU (1 equivalent) added. The reaction was stirred for up to one hour and before the resin was collected by filtration and washed 6 times with DMF and used directly in the next step. The next step was either reaction H or reaction J depending on the target sequence.

Reaction J:

The peptide was cleaved from the resin by treatment with 90% trifluoroacetic acid with 2.5% water, 2.5% triisopropylsilane and 5% dichloromethane. The resin was removed by filtration and the peptide accrued by precipitation with ice cold diethyl ether and collection by centrifugation. The crude peptide was then purified as detailed below.

Purification

The crude peptides were individually dissolved in acetonitrile/$H_2O$ (1:1, v/v) and purified by preparative HPLC with a C18 column using a water (0.1% TFA)-acetonitrile (0.1% TFA) gradient. The final purity of the peptides was confirmed by analytical HPLC. Peptide was lyophilized before storage at −20° C.

Compound Analysis—Identity and Purity

Analysis Method A

For analysis, the compounds were dissolved in methanol:water (9:1, 0.1 mg/ml) and a 150 µl portion was placed in an HPLC microvial and centrifuged at 14000 rpm for 3 minutes. The sample was then examined by high performance liquid chromatography with diode array (HPLC-DAD) and mass spectrometry (HPLC-MS) detection. HPLCDAD-MS was performed using an Agilent 1100 HPLC system comprising of quaternary pump, auto sampler, column oven and diode array detector coupled to a Waters ZQ single quadrupole mass spectrometer. The same reverse-phase Waters Xselect CSH C18, 2.1 mm×50 mm, 3.5 µm particle size column was used for all compounds and was fitted with a Waters VanGuard CSH C18, 2.1 mm×5 mm, 3.5 µm particle size guard column and Waters Acquity, 0.2 µm in-line column filter. The column was used at a flow rate of 1 ml/min maintained at a temperature of 60° C. The solvents used were 0.17% formic acid in 95% acetonitrile, 5% water (solvent B) and 10 mM ammonium formate, 0.2% formic acid in water (solvent A), with a gradient as follows: 5% solvent B from 0 to 0.2 min, 5 to 50% solvent B from 0.2 to 9.3 min, 50 to 95% solvent B from 9.3 to 9.5 min, 95% solvent B from 9.5 to 11 min, 95 to 5% solvent B from 11 to 11.05 min and re-equilibration with 5% solvent B from 11.05 to 11.5 min. Nitrogen was used as auxiliary and sheath gas. Source voltage was set at 3400 V, cone voltage set at 31 V with a gas flow of 50 L/hour, drying gas flow rate at 550 L/hour and drying gas temperature at 350° C.

Compound Analysis—Solubility and Stability in Solution

Analysis Method B

For solubility and stability analysis, the compounds were dissolved (0.2 mg/ml) in phosphate buffer solution (PBS, 10 mM, pH 7.4) and shaken at room temperature for 20 minutes. A T=0 hour sample was taken (80 µl) and centrifuged at 14000 rpm for 3 minutes then analysed by Analysis method A as above. The bulk samples were placed in a Techne Roller-Blot HB-3D Rolling Hybridiser at 37° C. and only removed when a sample (80 µl) was taken at time points T=4, 24 and 96 hours. The samples were centrifuged at 14000 rpm for 3 mins then analysed by HPLC-DAD-MS as above. The UV area under curve at 280 nm was recorded at each time point.

EXAMPLES

Example 1—Compound Synthesis

Compounds of the invention were made according to the methods set out in the General Synthesis Method.

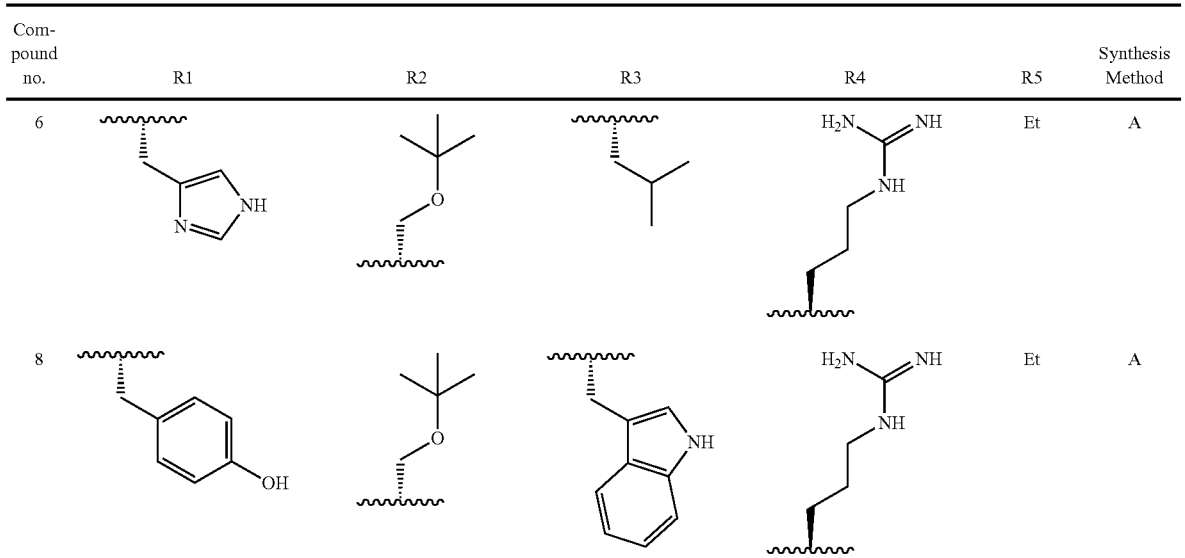

-continued

| Compound no. | R1 | R2 | R3 | R4 | R5 | Synthesis Method |
|---|---|---|---|---|---|---|
| 9 | 4-hydroxybenzyl | tert-butoxymethyl | isobutyl | 4-hydroxybenzyl | Et | A |
| 10 | imidazol-4-ylmethyl | tert-butoxymethyl | indol-3-ylmethyl | 3-guanidinopropyl | Et | A |
| 11 | imidazol-4-ylmethyl | tert-butoxymethyl | isobutyl | 4-hydroxybenzyl | Et | A |
| 12 | 4-hydroxybenzyl | tert-butoxymethyl | indol-3-ylmethyl | 4-hydroxybenzyl | Et | A |
| 13 | imidazol-4-ylmethyl | tert-butoxymethyl | indol-3-ylmethyl | 4-hydroxybenzyl | Et | A |
| 14 | 4-hydroxybenzyl | indol-3-ylmethyl | isobutyl | 4-hydroxybenzyl | $CH_2CONH_2$ | B |
| 16 | imidazol-4-ylmethyl | indol-3-ylmethyl | isobutyl | 4-hydroxybenzyl | $CH_2CONH_2$ | B |
| 20 | imidazol-4-ylmethyl | indol-3-ylmethyl | indol-3-ylmethyl | 3-guanidinopropyl | $CH_2CONH_2$ | B |

-continued

| Compound no. | R1 | R2 | R3 | R4 | R5 | Synthesis Method |
|---|---|---|---|---|---|---|
| 23 | imidazol-4-ylmethyl | naphthalen-2-ylmethyl | isobutyl | (CH₂)₃NHC(=NH)NH₂ | CH₂CONH₂ | B |
| 24 | 4-hydroxybenzyl | naphthalen-2-ylmethyl | 1H-indol-3-ylmethyl | (CH₂)₃NHC(=NH)NH₂ | CH₂CONH₂ | B |
| 25 | 4-hydroxybenzyl | naphthalen-2-ylmethyl | isobutyl | 4-hydroxybenzyl | CH₂CONH₂ | B |
| 27 | imidazol-4-ylmethyl | naphthalen-2-ylmethyl | 1H-indol-3-ylmethyl | (CH₂)₃NHC(=NH)NH₂ | CH₂CONH₂ | B |
| 28 | imidazol-4-ylmethyl | naphthalen-2-ylmethyl | isobutyl | 4-hydroxybenzyl | CH₂CONH₂ | B |
| 30 | 4-hydroxybenzyl | naphthalen-2-ylmethyl | 1H-indol-3-ylmethyl | 4-hydroxybenzyl | CH₂CONH₂ | B |
| 33 | imidazol-4-ylmethyl | naphthalen-2-ylmethyl | 1H-indol-3-ylmethyl | 4-hydroxybenzyl | CH₂CONH₂ | B |

-continued

| Compound no. | R1 | R2 | R3 | R4 | R5 | Synthesis Method |
|---|---|---|---|---|---|---|
| 42 | CH2-(1H-imidazol-4-yl) | isobutyl | isobutyl | -(CH2)3-NH-C(=NH)-NH2 | Et | A |
| 44 | CH2-(4-hydroxyphenyl) | isobutyl | CH2-(1H-indol-3-yl) | -(CH2)3-NH-C(=NH)-NH2 | Et | A |
| 45 | CH2-(4-hydroxyphenyl) | isobutyl | isobutyl | CH2-(4-hydroxyphenyl) | Et | A |
| 47 | CH2-(1H-imidazol-4-yl) | isobutyl | CH2-(1H-indol-3-yl) | -(CH2)3-NH-C(=NH)-NH2 | Et | A |
| 48 | CH2-(1H-imidazol-4-yl) | isobutyl | isobutyl | CH2-(4-hydroxyphenyl) | Et | A |
| 49 | CH2-(4-hydroxyphenyl) | isobutyl | CH2-(1H-indol-3-yl) | CH2-(4-hydroxyphenyl) | Et | A |
| 50 | CH2-(1H-imidazol-4-yl) | isobutyl | CH2-(1H-indol-3-yl) | CH2-(4-hydroxyphenyl) | Et | A |

-continued

| Compound no. | R1 | R2 | R3 | R4 | R5 | Synthesis Method |
|---|---|---|---|---|---|---|
| 56 | 4-imidazolylmethyl | 1-benzyl-4-imidazolylmethyl | isobutyl | 4-guanidinobutyl | Et | A |
| 59 | 4-hydroxybenzyl | 1-benzyl-4-imidazolylmethyl | isobutyl | 4-hydroxybenzyl | Et | A |
| 60 | 4-imidazolylmethyl | 1-benzyl-4-imidazolylmethyl | 3-indolylmethyl | 4-guanidinobutyl | Et | A |
| 61 | 4-imidazolylmethyl | 1-benzyl-4-imidazolylmethyl | isobutyl | 4-hydroxybenzyl | Et | A |
| 62 | 4-hydroxybenzyl | 1-benzyl-4-imidazolylmethyl | 3-indolylmethyl | 4-hydroxybenzyl | Et | A |

-continued

| Compound no. | R1 | R2 | R3 | R4 | R5 | Synthesis Method |
|---|---|---|---|---|---|---|
| 63 | imidazole-CH2- | N-benzyl imidazole-CH2- | indole-CH2- | 4-hydroxyphenyl-CH2- | Et | A |
| 64 | 4-hydroxyphenyl-CH2- | indole-CH2- | indole-CH2- | 4-hydroxyphenyl-CH2- | CH2CONH2 | |
| 65 | imidazole-CH2- | indole-CH2- | indole-CH2- | 4-hydroxyphenyl-CH2- | CH2CONH2 | |
| 66 | 4-hydroxyphenyl-CH2- | indole-CH2- | indole-CH2- | guanidino-propyl- | CH2CONH2 | |
| 67 | 4-hydroxyphenyl-CH2- | N-benzyl imidazole-CH2- | indole-CH2- | guanidino-propyl- | Et | |
| 68 | imidazole-CH2- | indole-CH2- | isobutyl | guanidino-propyl- | CH2CONH2 | |

| Compound number | Salt form | Retention Time (Analysis method A) | m/z (Analysis method A) |
| --- | --- | --- | --- |
| 6 | TFA | 4.15 | 1213.8 |
| 8 | TFA | 5.5 | 1312.7 |
| 9 | TFA | 6.64 | 1246.8 |
| 10 | TFA | 4.27 | 1286.9 |
| 11 | TFA | 5.35 | 1220.9 |
| 12 | TFA | 6.75 | 1319.7 |
| 13 | TFA | 5.53 | 1293.7 |
| 14 | TFA | 6.13 | 1318.7 |
| 16 | TFA | 4.93 | 1292.8 |
| 20 | TFA | 4.02 | 1358.9 |
| 23 | TFA | 4.79 | 1296.7 |
| 24 | TFA | 5.84 | 1395.7 |
| 25 | TFA | 7.19 | 1329.6 |
| 27 | TFA | 4.91 | 1369.6 |
| 28 | TFA | 5.92 | 1303.8 |
| 30 | TFA | 7.20 | 1402.7 |
| 33 | TFA | 6.00 | 1376.4 |
| 42 | TFA | 3.90 | 1183.8 |
| 44 | TFA | 5.23 | 1282.8 |
| 45 | TFA | 6.35 | 1216.8 |
| 47 | TFA | 4.00 | 1256.8 |
| 48 | TFA | 5.12 | 1190.8 |
| 49 | TFA | 6.56 | 1290.0 |
| 50 | TFA | 5.30 | 1263.7 |
| 56 | TFA | 3.42 | 1297.7 |
| 59 | TFA | 5.22 | 1330.8 |
| 60 | TFA | 3.81 | 1370.6 |
| 61 | TFA | 4.36 | 1304.7 |
| 62 | TFA | 5.60 | 1403.5 |
| 63 | TFA | 4.69 | 1377.7 |
| 64 | TFA | 6.19 | 1391.7 |
| 65 | TFA | 5.09 | 1366.0 |
| 66 | TFA | 4.92 | 1384.7 |
| 67 | TFA | 4.47 | 1396.9 |
| 68 | TFA | 3.83 | 1285.8 |

Example 2—Solubility Analysis

The solubility of compounds of the invention was tested as described in the general methods. Solubility was then graded according to a rating between 1 to 5, where 1 is most soluble and 5 is least soluble.

| Compound number | Solubility grading |
| --- | --- |
| Buserelin acetate | 1 |
| Triptorelin acetate | 2 |
| Naferelin acetate | 2 |
| Histrelin acetate | 4 |
| Leuprorelin acetate | 2 |
| Buserelin TFA | 2 |
| Triptorelin TFA | 2 |
| Naferelin TFA | 1 |
| Histrelin TFA | 2 |
| Leuprorelin TFA | 1 |
| 6 | 1 |
| 8 | 2 |
| 9 | 1 |
| 10 | 1 |
| 11 | 1 |
| 12 | 4 |
| 13 | 3 |
| 14 | 4 |
| 16 | 2 |
| 20 | 3 |
| 23 | 1 |
| 24 | 5 |
| 25 | 4 |
| 33 | 2 |
| 30 | 1 |
| 28 | 2 |
| 27 | 1 |
| 56 | 1 |
| 67 | 1 |
| 59 | 4 |
| 63 | 5 |
| 62 | 5 |
| 61 | 3 |
| 60 | 2 |
| 42 | 1 |
| 44 | 2 |
| 45 | 2 |
| 50 | 1 |
| 49 | 4 |
| 48 | 2 |
| 47 | 1 |
| 68 | 1 |
| 66 | 5 |
| 14 | 4 |
| 65 | 4 |
| 64 | 5 |
| 16 | 2 |
| 20 | 3 |

Example 3—Stability Analysis

The stability of compounds of the invention in aqueous media (PBS ph7.4) was tested as described in the general methods. Stability was then graded according to a rating where t1/2>96 minutes was shown as + and stability less than this was shown as −.

| Compound number | Stability grading |
| --- | --- |
| 6 | + |
| 8 | + |
| 9 | + |
| 10 | + |
| 11 | + |
| 12 | + |
| 13 | + |
| 14 | + |
| 16 | + |
| 20 | + |
| 23 | + |
| 24 | − |
| 25 | − |
| 33 | − |
| 30 | − |
| 28 | + |
| 27 | + |
| 56 | + |
| 67 | − |
| 59 | − |
| 63 | − |
| 62 | − |
| 61 | + |
| 60 | + |
| 42 | + |
| 44 | + |
| 45 | + |
| 50 | + |
| 49 | + |
| 48 | + |
| 47 | + |
| 68 | + |
| 66 | + |
| 14 | + |
| 65 | + |
| 64 | − |
| 16 | + |
| 20 | + |

Example 4—GnRH R Stimulation

The ability of compounds of the invention to stimulate GnRHR was assessed by using a calcium assay with CHO-K1 cells (Genscript), see the general methods for details. Activity was then recorded as percentage stimulation at 1 µM.

| Compound number | GNRHR Stimulation at 1 µM |
|---|---|
| Buserelin | 94 |
| Leuprorelin | 107 (n = 2) |
| Goserelin | 99 |
| Gonadorelin | 102 |
| Nafarelin | 100 (n = 2) |
| 6 | 88 |
| 8 | 86 |
| 9 | 78 |
| 10 | 81 |
| 11 | 76 |
| 12 | 80 |
| 13 | 87 |
| 14 | 78 |
| 16 | 76 |
| 20 | 75 |
| 23 | 106 |
| 24 | 87 |
| 25 | 82 |
| 33 | 67 |
| 30 | 12 |
| 28 | 95 |
| 27 | 108 |
| 56 | 96 |
| 67 | 117 |
| 59 | 85 |
| 63 | 77 |
| 62 | 77 |
| 61 | 112 |
| 60 | 102 |
| 42 | 102 |
| 44 | 111 |
| 45 | 105 |
| 50 | 105 |
| 49 | 77 |
| 48 | 118 |
| 47 | 119 |
| 68 | 86 |
| 66 | 83 |
| 14 | 78 |
| 65 | 72 |
| 64 | 50 |
| 16 | 76 |
| 20 | 75 |

REFERENCES

Interferon-inducible effector mechanisms in cellautonomous immunity. MacMicking, J. D. Nat. Rev. Immunol. 12, 367-382 (2012).

Toll-like receptor 2-dependent inhibition of macrophage class II MHC expression and antigen processing by 19-kDa lipoprotein of *Mycobacterium tuberculosis*. Noss, E. H. et al. J. Immunol. 167, 910-918 (2001).

HIV-1 Nef-induced Down-Regulation of MHC Class I Requires AP-1 and Clathrin but Not PACS-1 and Is Impeded by AP-2. Lubben, N. B. et al. Mol Biol. Cell. 18 (3351-3365).

Processing of *Mycobacterium tuberculosis* antigen 85B involves intraphagosomal formation of peptide-major histocompatibility complex II complexes and is inhibited by live bacilli that decrease phagosome maturation. Ramachandra, L., Noss, E., Boom, W. H. & Harding, C. V. J. Exp. Med. 194, 1421-1432 (2001).

The ins and outs of MHC class II-mediated antigen processing and presentation. Paul A. Roche & Kazuyuki Furuta. *Nature Reviews Immunology* 15, 203-216 (2015)

Secreted *Toxoplasma gondii* molecules interfere with expression of MHC-II in interferon gamma-activated macrophages. Leroux L-P, Dasanayake D, Rommerein L M, Fox B A, Bzik D J, Jardim A, Dzierszinski F S. *International Journal for Parasitology* 2015 45: 319-332

Protection form Direct Cerebral *Cryptococcus* Infection by Interferon gamma-dependent Activation of Microglial Cells. Zhou Q, Gault R A, Kozel T R, Murphy W J. *The Journal of Immunology* 2007: 178: 5753-5761.

*Mycobacterium tuberculosis* EsxH inhibits ESCRT-dependent CD4+ T-cell activation Portal-Celhay C, Tufariello J A M, Srivastava S, Zahra A, Klevorn T, Grace P S, Mehra A, Park H S, Ernst J D, Jacobs Jr W R & Philips J A. *Nature Microbiology* 2, Article number: 16232 (2016) doi:10.1038/nmicrobiol.2016.232

Gonadotropin secretion and its control. Fink G, The physiology of reproduction 1998.

Immunomodulatory actions of gonadal steroids may be mediated by gonadotropin-releasing hormone. Jacobson J D and Ansari M A, Endocrinology 2004; 145(1):330-6.

Unusual morphologic features of uterine leiomyomas treated with gonadotropin-releasing hormoneagonists: massive lymphoid infiltration and vasculitis. McClean G and McCluggage W G, Int J Surg Pathol. 2003; 11(4): 339-44.

Massive lymphocytic infiltration of uterine leyomyomas associated with GnRH agonist treatment. Bardsley V et al., Histopathology 1998; 33(1):80-2.

Chronic plasma cell endometritis in hysterectomy specimens of HIV-infected women: a retrospective analysis. Kerr-Layton J A et al., Infect Dis Obstet Gynecol. 1998; 6(4):186-90.

Serum dihydrotestosterone and testosterone concentrations in human immunodeficiency virus-infected men with and without weight loss. Arver S et al., J Androl 1999; 20(5):611-8.

Prevalence of endocrine dysfunction in HIV-infected men. Brockmeyer G et al., Horm Res 2000; 54(5-6):294-5.

Gonadotropin-releasing hormone increases CD4-T-lymphocyte numbers in an animal model of immunodeficiency. Jacobson J D et al., J Allergy Clin Immunol. 1999; 104:653-8.

A transcriptionally active human type II gonadotropin-releasing hormone receptor gene homolog overlaps two genes in the antisense orientation on chromosome 1q.12. Morgan et al., Endocrinology. 2003 February; 144(2): 423-36

Gonadotropin-releasing hormone (GnRH)-binding sites in human breast cancer cell lines and inhibitory effects of GnRH antagonists. Eidne et al., J Olin Endocrinol Metab. 1987 March; 64(3):425-32

All references referred to in this application, including patent and patent applications, are incorporated herein by reference to the fullest extent possible.

The invention claimed is:

1. A GnRH analog according to formula (I):

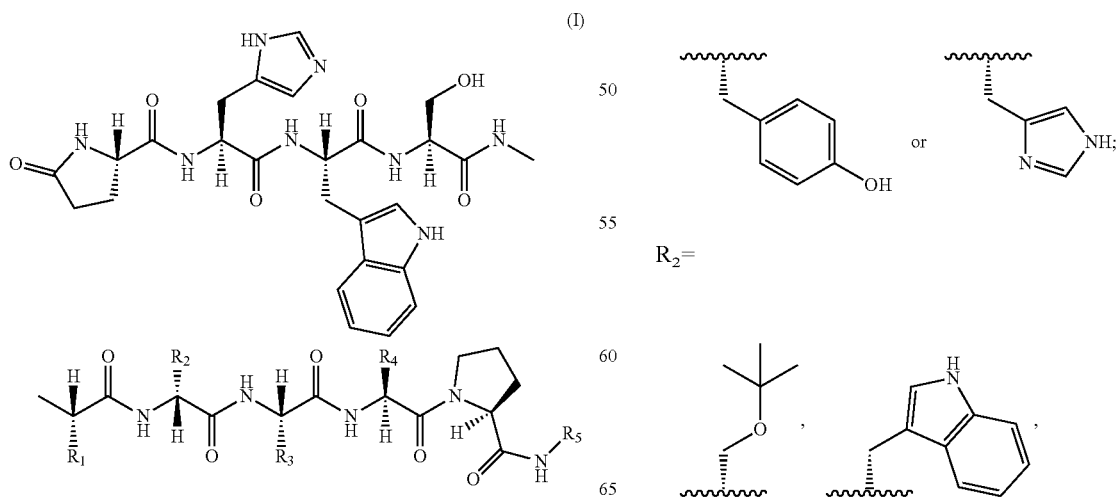

or a pharmaceutically acceptable salt thereof; wherein $R_1$=

$R_2$=

-continued $R_3=$

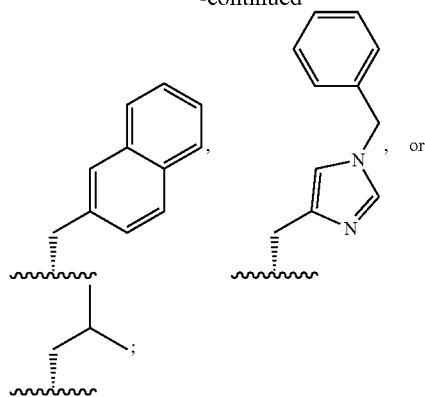

$R_4=$

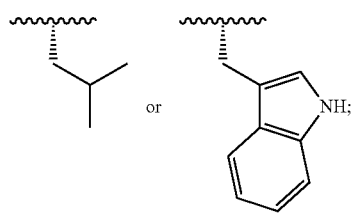

$R_5$=Me, Et, $CH_2CF_3$, iPr, nPr, nBu, iBu, sBu, tBu, cyclopropyl, $CH_2CONH_2$, or $NHCONH_2$; and wherein one of $R_1$, $R_3$, and $R_4$ is selected from Type I according to the list below, and two of $R_1$, $R_3$, and $R_4$ are selected from Type II according to the list below:

| Group | Type I | Type II |
|---|---|---|
| $R_1$ | | |
| $R_3$ | | |

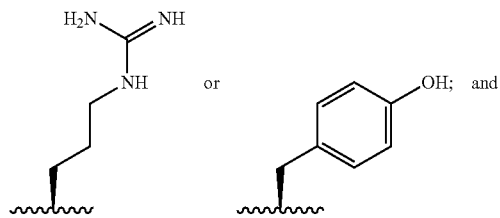

-continued

| Group | Type I | Type II |
|---|---|---|
| $R_4$ | | |

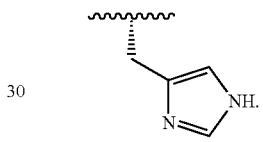

2. The GnRH analog according to claim 1, wherein $R_5$=Et or $CH_2CONH_2$.

3. The GnRH analog according to claim 1, wherein $R_5$=Me, iPr, nPr, nBu, iBu, sBu, or tBu.

4. A pharmaceutical composition comprising a GnRH analog according to claim 1 and one or more pharmaceutically acceptable excipients.

5. The GnRH analog according to claim 1, wherein $R_1=$

6. The GnRH analog according to claim 5, wherein:

$R_2=$

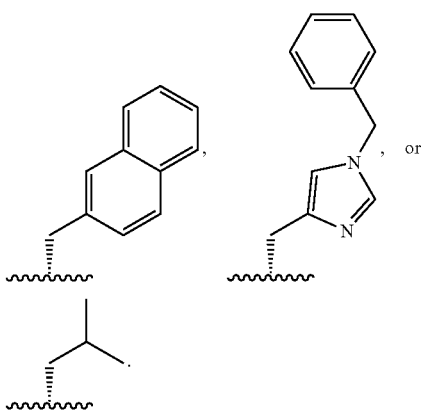

7. The GnRH analog according to claim 5, wherein:

$R_1=$ $R_3=$ 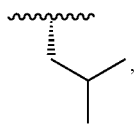, and $R_4=$ 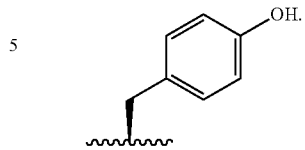

8. The GnRH analog according to claim 7, wherein the GnRH analog according to formula (I) is one of the following compounds:

| Compound no. | $R_1$ | $R_2$ | $R_3$ | $R_4$ | $R_5$ |
|---|---|---|---|---|---|
| 28 | imidazole-CH₂- | naphthyl-CH₂- | isobutyl | 4-hydroxybenzyl | $CH_2CONH_2$ |
| 35 | imidazole-CH₂- | naphthyl-CH₂- | isobutyl | 4-hydroxybenzyl | Et |
| 55 | imidazole-CH₂- | N-benzylimidazole-CH₂- | isobutyl | 4-hydroxybenzyl | $CH_2CONH_2$ |
| 61 | imidazole-CH₂- | N-benzylimidazole-CH₂- | isobutyl | 4-hydroxybenzyl | Et |

-continued

| Compound no. | R₁ | R₂ | R₃ | R₄ | R₅ |
|---|---|---|---|---|---|
| 41 | imidazolylmethyl | isobutyl | isobutyl | 4-hydroxybenzyl | CH₂CONH₂ |
| 48 | imidazolylmethyl | isobutyl | isobutyl | 4-hydroxybenzyl | Et | or a pharmaceutically acceptable salt of any of these.

9. The GnRH analog according to claim 5, wherein:

$R_1 =$

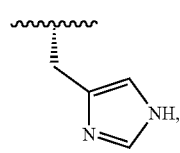

$R_3 =$

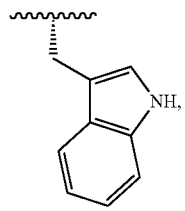

and $R_4 =$

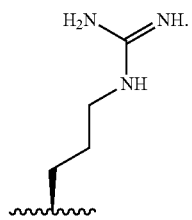

10. The GnRH analog according to claim 9, wherein the GnRH analog according to formula (I) is one of the following compounds:

| Compound no. | R₁ | R₂ | R₃ | R₄ | R₅ |
|---|---|---|---|---|---|
| 27 | imidazolylmethyl | naphthylmethyl | indolylmethyl | guanidinopropyl | CH₂CONH₂ |
| 34 | imidazolylmethyl | naphthylmethyl | indolylmethyl | guanidinopropyl | Et |

-continued
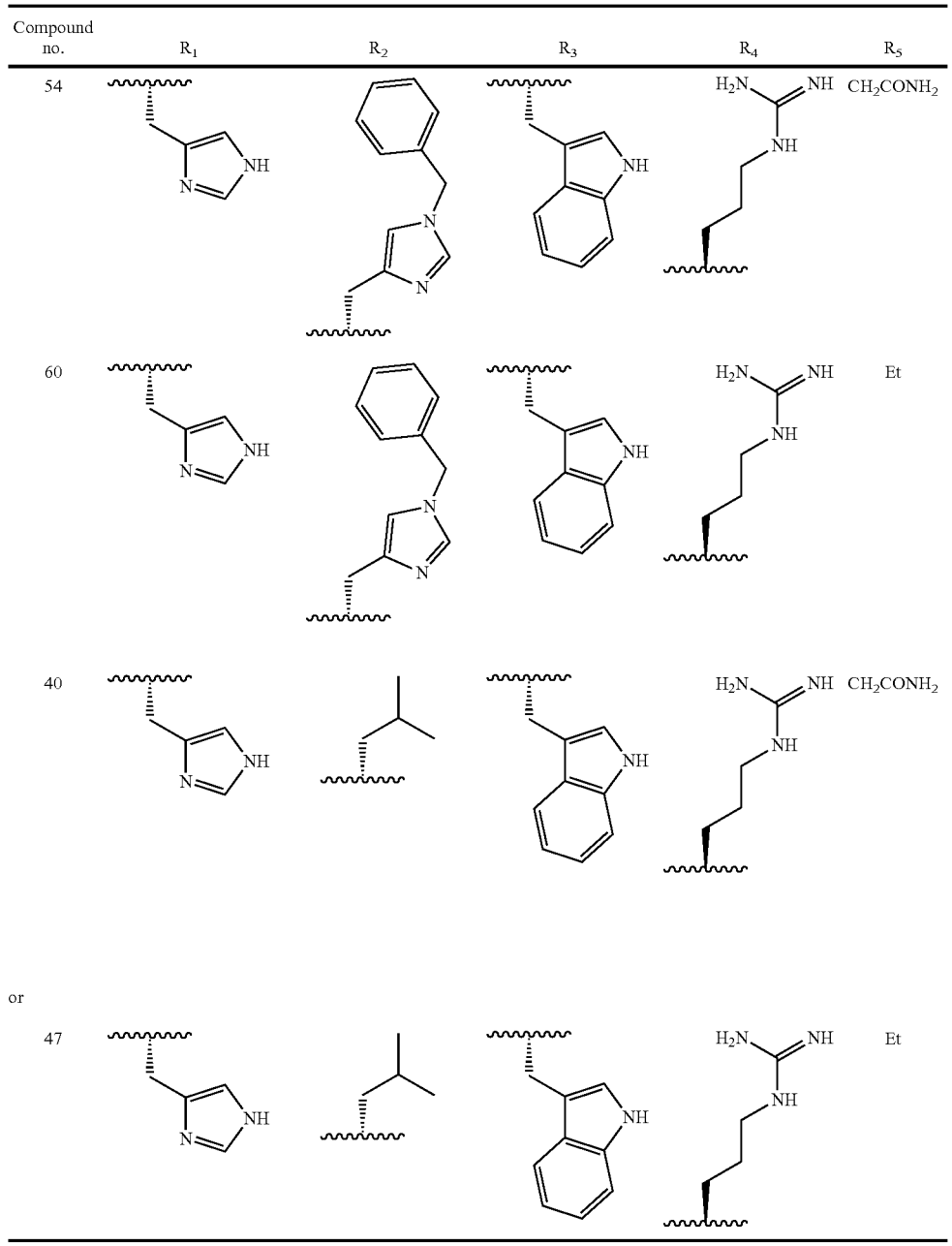
or a pharmaceutically acceptable salt of any of these.
11. The GnRH analog according to claim 5, wherein $R_2=$
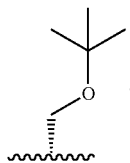
12. The GnRH analog according to claim 11, wherein the GnRH analog according to formula (I) is one of the following compounds:

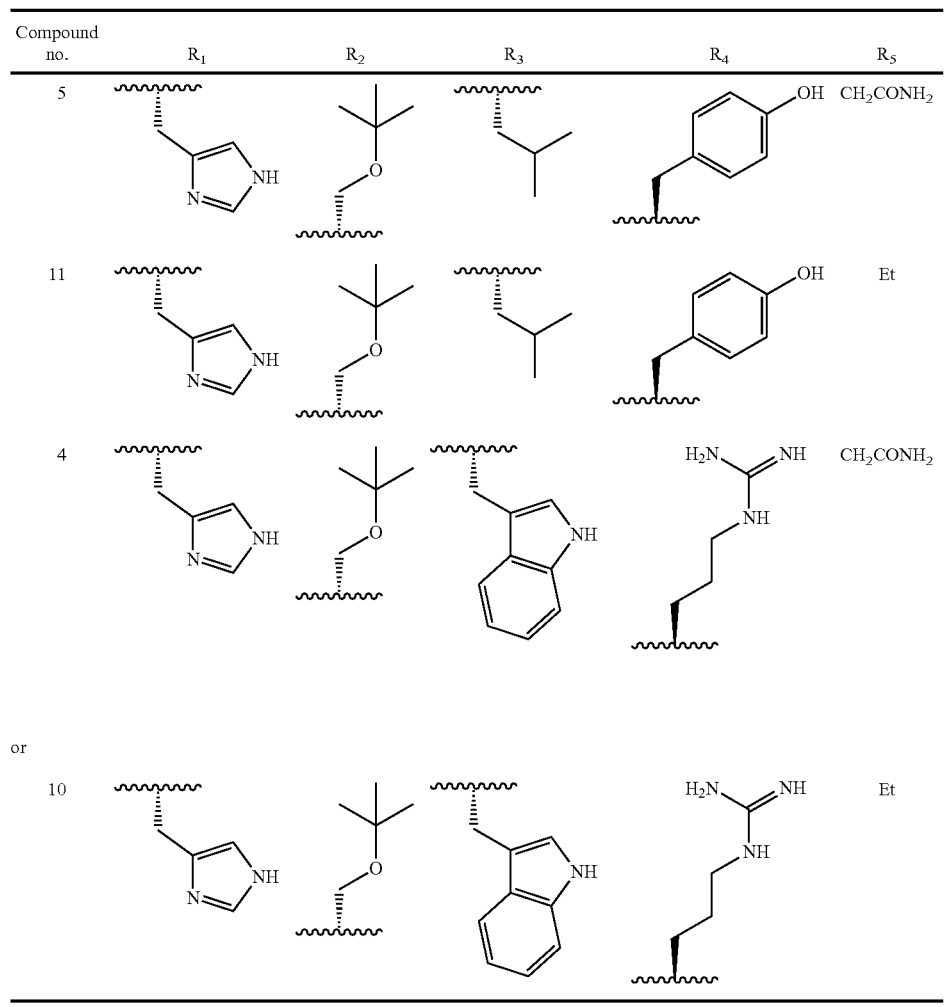
or a pharmaceutically acceptable salt of any of these.
13. The GnRH analog according to claim 1, wherein:
$R_1 =$
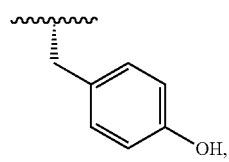
$R_3 =$
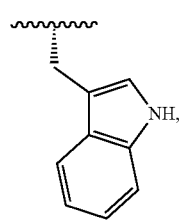
and $R_4 =$
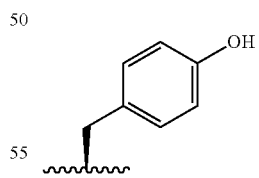
14. The GnRH analog according to claim 13, wherein the GnRH analog according to formula (I) is one of the following compounds:

| Compound no. | R₁ | R₂ | R₃ | R₄ | R₅ |
|---|---|---|---|---|---|
| 7 | 4-hydroxybenzyl | tert-butoxymethyl | (1H-indol-3-yl)methyl | 4-hydroxybenzyl | CH₂CONH₂ |
| 12 | 4-hydroxybenzyl | tert-butoxymethyl | (1H-indol-3-yl)methyl | 4-hydroxybenzyl | Et |
| 30 | 4-hydroxybenzyl | naphthalen-2-ylmethyl | (1H-indol-3-yl)methyl | 4-hydroxybenzyl | CH₂CONH₂ |
| 36 | 4-hydroxybenzyl | naphthalen-2-ylmethyl | (1H-indol-3-yl)methyl | 4-hydroxybenzyl | Et |
| 62 | 4-hydroxybenzyl | (1-benzyl-1H-imidazol-4-yl)methyl | (1H-indol-3-yl)methyl | 4-hydroxybenzyl | Et |
| 43 | 4-hydroxybenzyl | isobutyl | (1H-indol-3-yl)methyl | 4-hydroxybenzyl | CH₂CONH₂ |

| Compound no. | R₁ | R₂ | R₃ | R₄ | R₅ |
|---|---|---|---|---|---|
| or 49 | 4-hydroxybenzyl | isobutyl | indol-3-ylmethyl | 4-hydroxyphenethyl | Et | or a pharmaceutically acceptable salt of any of these.

15. A GnRH analog or a pharmaceutically acceptable salt thereof, wherein the GnRH analog is one of the following compounds:

1: pGlu-His-Trp-Ser-His-D-Ser(tBu)-Leu-Arg-Pro-Gly-NH₂,
2: pGlu-His-Trp-Ser-Tyr-D-Ser(tBu)-Trp-Arg-Pro-Gly-NH₂,
3: pGlu-His-Trp-Ser-Tyr-D-Ser(tBu)-Leu-Tyr-Pro-Gly-NH₂,
6: pGlu-His-Trp-Ser-His-D-Ser(tBu)-Leu-Arg-Pro-NHEt,
8: pGlu-His-Trp-Ser-Tyr-D-Ser(tBu)-Trp-Arg-Pro-NHEt,
9: pGlu-His-Trp-Ser-Tyr-D-Ser(tBu)-Leu-Tyr-Pro-NHEt,
23: pGlu-His-Trp-Ser-His-D-Nal-Leu-Arg-Pro-Gly-NH₂,
24: pGlu-His-Trp-Ser-Tyr-D-Nal-Trp-Arg-Pro-Gly-NH₂,
25: pGlu-His-Trp-Ser-Tyr-D-Nal-Leu-Tyr-Pro-Gly-NH₂,
26: pGlu-His-Trp-Ser-Tyr-D-Nal-Leu-Arg-Pro-NHEt,
29: pGlu-His-Trp-Ser-His-D-Nal-Leu-Arg-Pro-NHEt,
31: pGlu-His-Trp-Ser-Tyr-D-Nal-Trp-Arg-Pro-NHEt,
32: pGlu-His-Trp-Ser-Tyr-D-Nal-Leu-Tyr-Pro-NHEt
33: pGlu-His-Trp-Ser-His-D-Nal-Trp-Tyr-Pro-Gly-NH₂,
37: pGlu-His-Trp-Ser-His-D-Leu-Leu-Arg-Pro-Gly-NH₂,
38: pGlu-His-Trp-Ser-Try-D-Leu-Trp-Arg-Pro-Gly-NH₂,
39: pGlu-His-Trp-Ser-Tyr-D-Leu-Leu-Tyr-Pro-Gly-NH₂,
42: pGlu-His-Trp-Ser-His-D-Leu-Leu-Arg-Pro-NHEt,
44: pGlu-His-Trp-Ser-Tyr-D-Leu-Trp-Arg-Pro-NHEt,
45: pGlu-His-Trp-Ser-Tyr-D-Leu-Leu-Tyr-Pro-NHEt,
50: pGlu-His-Trp-Ser-His-D-Leu-Trp-Tyr-Pro-NHEt,
51: pGlu-His-Trp-Ser-His-D-Bhi-Leu-Arg-Pro-Gly-NH₂,
52: pGlu-His-Trp-Ser-Tyr-D-Bhi-Trp-Arg-Pro-Gly-NH₂,
53: pGlu-His-Trp-Ser-Tyr-D-Bhi-Leu-Tyr-Pro-Gly-NH₂,
56: pGlu-His-Trp-Ser-His-D-Bhi-Leu-Arg-Pro-NHEt,
57: pGlu-His-Trp-Ser-Tyr-D-Bhi-Trp-Arg-Pro-Gly-NH₂,
58: pGlu-His-Trp-Ser-Tyr-D-Bhi-Trp-Arg-Pro-Gly-NH₂,
59: pGlu-His-Trp-Ser-Tyr-D-Bhi-Leu-Tyr-Pro-NHEt,
63: pGlu-His-Trp-Ser-His-D-Bhi-Trp-Tyr-Pro-NHEt, or
67: pGlu-His-Trp-Ser-Tyr-D-Bhi-Trp-Arg-Pro-NHEt.

* * * * *

UNITED STATES PATENT AND TRADEMARK OFFICE
CERTIFICATE OF CORRECTION

PATENT NO. : 11,564,969 B2
APPLICATION NO. : 16/479520
DATED : January 31, 2023
INVENTOR(S) : Ola Winqvist et al.

Page 1 of 1

It is certified that error appears in the above-identified patent and that said Letters Patent is hereby corrected as shown below:

In the Claims

In Column 108, Claim 1, Lines 60-65, delete " 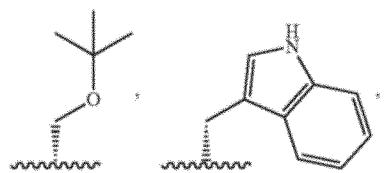 " and insert

-- 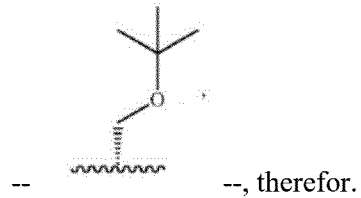 --, therefor.

Signed and Sealed this
Eleventh Day of April, 2023

Katherine Kelly Vidal
Director of the United States Patent and Trademark Office

SEQUENCE LISTING

```
<160> NUMBER OF SEQ ID NOS: 95

<210> SEQ ID NO 1
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 1

Glu His Trp Ser His Ser Leu Arg Pro Gly
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 2

Glu His Trp Ser Tyr Ser Trp Arg Pro Gly
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 3

Glu His Trp Ser Tyr Ser Leu Tyr Pro Gly
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 4

Glu His Trp Ser His Ser Trp Arg Pro Gly
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 5

Glu His Trp Ser His Ser Leu Tyr Pro Gly
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 6

Glu His Trp Ser His Ser Leu Arg Pro
1               5
```

<210> SEQ ID NO 7
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 7

Glu His Trp Ser Tyr Ser Trp Tyr Pro Gly
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 8

Glu His Trp Ser Tyr Ser Trp Arg Pro
1               5

<210> SEQ ID NO 9
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 9

Glu His Trp Ser Tyr Ser Leu Tyr Pro
1               5

<210> SEQ ID NO 10
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 10

Glu His Trp Ser His Ser Trp Arg Pro
1               5

<210> SEQ ID NO 11
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 11

Glu His Trp Ser His Ser Leu Tyr Pro
1               5

<210> SEQ ID NO 12
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 12

Glu His Trp Ser Tyr Ser Trp Tyr Pro
1               5

```
<210> SEQ ID NO 13
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 13

Glu His Trp Ser His Ser Trp Tyr Pro
1               5

<210> SEQ ID NO 14
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 14

Glu His Trp Ser Tyr Trp Leu Tyr Pro Gly
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 15

Glu His Trp Ser Tyr Trp Leu Arg Pro
1               5

<210> SEQ ID NO 16
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 16

Glu His Trp Ser His Trp Leu Tyr Pro Gly
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 17

Glu His Trp Ser His Trp Leu Arg Pro
1               5

<210> SEQ ID NO 18
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 18

Glu His Trp Ser Tyr Trp Trp Arg Pro
1               5
```

```
<210> SEQ ID NO 19
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 19

Glu His Trp Ser Tyr Trp Leu Tyr Pro
1               5

<210> SEQ ID NO 20
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 20

Glu His Trp Ser His Trp Trp Arg Pro
1               5

<210> SEQ ID NO 21
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 21

Glu His Trp Ser His Trp Leu Tyr Pro
1               5

<210> SEQ ID NO 22
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 22

Glu His Trp Ser Tyr Trp Trp Tyr Pro
1               5

<210> SEQ ID NO 23
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 23

Glu His Trp Ser His Phe Leu Arg Pro Gly
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 24

Glu His Trp Ser Tyr Phe Trp Arg Pro Gly
1               5                   10

<210> SEQ ID NO 25
```

```
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 25

Glu His Trp Ser Tyr Phe Leu Tyr Pro Gly
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 26

Glu His Trp Ser Tyr Phe Leu Arg Pro
1               5

<210> SEQ ID NO 27
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 27

Glu His Trp Ser His Phe Trp Arg Pro Gly
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 28

Glu His Trp Ser His Phe Leu Tyr Pro Gly
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 29

Glu His Trp Ser His Phe Leu Arg Pro
1               5

<210> SEQ ID NO 30
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 30

Glu His Trp Ser Tyr Phe Trp Tyr Pro Gly
1               5                   10

<210> SEQ ID NO 31
<211> LENGTH: 9
```

```
<212> TYPE: PRT
<213> ORGANISM: Artificial Sequence
<220> FEATURE:
<223> OTHER INFORMATION: Man-made analogue of GnRH II

<400> SEQUENCE: 31

Glu His Trp Ser Tyr Phe Trp Arg Pro
1               5

<210> SEQ ID NO 32
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 32

Glu His Trp Ser Tyr Phe Leu Tyr Pro
1               5

<210> SEQ ID NO 33
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 33

Glu His Trp Ser His Phe Trp Tyr Pro Gly
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 34

Glu His Trp Ser His Phe Trp Arg Pro
1               5

<210> SEQ ID NO 35
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 35

Glu His Trp Ser His Phe Leu Tyr Pro
1               5

<210> SEQ ID NO 36
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 36

Glu His Trp Ser Tyr Phe Trp Tyr Pro
1               5

<210> SEQ ID NO 37
<211> LENGTH: 10
<212> TYPE: PRT
```

```
<213> ORGANISM: Artificial Sequence
<220> FEATURE:
<223> OTHER INFORMATION: Man-made analogue of GnRH II

<400> SEQUENCE: 37

Glu His Trp Ser His Leu Leu Arg Pro Gly
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 38

Glu His Trp Ser Tyr Leu Trp Arg Pro Gly
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 39

Glu His Trp Ser Tyr Leu Leu Tyr Pro Gly
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 40

Glu His Trp Ser His Leu Trp Arg Pro Gly
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 41

Glu His Trp Ser His Leu Leu Tyr Pro Gly
1               5                   10

<210> SEQ ID NO 42
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 42

Glu His Trp Ser His Leu Leu Arg Pro
1               5

<210> SEQ ID NO 43
<211> LENGTH: 10
<212> TYPE: PRT
<213> ORGANISM: Artificial Sequence
```

```
<220> FEATURE:
<223> OTHER INFORMATION: Man-made analogue of GnRH II

<400> SEQUENCE: 43

Glu His Trp Ser Tyr Leu Trp Tyr Pro Gly
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 44

Glu His Trp Ser Tyr Leu Trp Arg Pro
1               5

<210> SEQ ID NO 45
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 45

Glu His Trp Ser Tyr Leu Leu Tyr Pro
1               5

<210> SEQ ID NO 46
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 46

Glu His Trp Ser His Leu Trp Tyr Pro Gly
1               5                   10

<210> SEQ ID NO 47
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 47

Glu His Trp Ser His Leu Trp Arg Pro
1               5

<210> SEQ ID NO 48
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 48

Glu His Trp Ser His Leu Leu Tyr Pro
1               5

<210> SEQ ID NO 49
<211> LENGTH: 9
<212> TYPE: PRT
<213> ORGANISM: Artificial Sequence
<220> FEATURE:
```

<223> OTHER INFORMATION: Man-made analogue of GnRH II

<400> SEQUENCE: 49

Glu His Trp Ser Tyr Leu Trp Tyr Pro
1               5

<210> SEQ ID NO 50
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 50

Glu His Trp Ser His Leu Trp Tyr Pro
1               5

<210> SEQ ID NO 51
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 51

Glu His Trp Ser His His Leu Arg Pro Gly
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 52

Glu His Trp Ser Tyr His Trp Arg Pro Gly
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 53

Glu His Trp Ser Tyr His Leu Tyr Pro Gly
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 54

Glu His Trp Ser His His Trp Arg Pro Gly
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 55

Glu His Trp Ser His His Leu Tyr Pro Gly
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 56

Glu His Trp Ser His His Leu Arg Pro
1               5

<210> SEQ ID NO 57
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 57

Glu His Trp Ser Tyr His Trp Arg Pro Gly
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 58

Glu His Trp Ser Tyr His Trp Arg Pro Gly
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 59

Glu His Trp Ser Tyr His Leu Tyr Pro
1               5

<210> SEQ ID NO 60
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 60

Glu His Trp Ser His His Trp Arg Pro
1               5

<210> SEQ ID NO 61
<211> LENGTH: 9
<212> TYPE: PRT
<213> ORGANISM: Artificial Sequence
<220> FEATURE:
<223> OTHER INFORMATION: Man-made analogue of GnRH II -continued

```
<400> SEQUENCE: 61

Glu His Trp Ser His His Leu Tyr Pro
1               5

<210> SEQ ID NO 62
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 62

Glu His Trp Ser Tyr His Trp Tyr Pro
1               5

<210> SEQ ID NO 63
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 63

Glu His Trp Ser His His Trp Tyr Pro
1               5

<210> SEQ ID NO 64
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 64

Glu His Trp Ser His Ser Trp Tyr Pro Gly
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 65

Glu His Trp Ser His Trp Leu Arg Pro Gly
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 66

Glu His Trp Ser Tyr Trp Trp Arg Pro Gly
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 67
```

```
Glu His Trp Ser His Trp Trp Arg Pro Gly
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 68

Glu His Trp Ser Tyr Trp Trp Tyr Pro Gly
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 69

Glu His Trp Ser His Trp Trp Tyr Pro Gly
1               5                   10

<210> SEQ ID NO 70
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 70

Glu His Trp Ser His Trp Trp Tyr Pro
1               5

<210> SEQ ID NO 71
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 71

Glu His Trp Ser His Phe Trp Tyr Pro
1               5

<210> SEQ ID NO 72
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 72

Glu His Trp Ser His Leu Trp Tyr Pro Gly
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 73
```

```
Glu His Trp Ser Tyr Trp Leu Arg Pro Gly
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 74

Glu His Trp Ser Tyr Phe Leu Arg Pro Gly
1               5                   10

<210> SEQ ID NO 75
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 75

Glu His Trp Ser Tyr Ser Leu Arg Pro
1               5

<210> SEQ ID NO 76
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 76

Glu His Trp Ser Tyr His Leu Arg Pro
1               5

<210> SEQ ID NO 77
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 77

Glu His Trp Ser Tyr Leu Leu Arg Pro
1               5

<210> SEQ ID NO 78
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 78

Glu His Trp Ser Tyr Ser Leu Arg Pro
1               5

<210> SEQ ID NO 79
<211> LENGTH: 10
<212> TYPE: PRT
<213> ORGANISM: Homo sapiens
<220> FEATURE:
<223> OTHER INFORMATION: GnRH I

<400> SEQUENCE: 79

Glu His Trp Ser Tyr Gly Leu Arg Pro Gly
```

<210> SEQ ID NO 80
<211> LENGTH: 10
<212> TYPE: PRT
<213> ORGANISM: Homo sapiens
<220> FEATURE:
<223> OTHER INFORMATION: GnRH II

<400> SEQUENCE: 80

Glu His Trp Ser His Gly Trp Tyr Pro Gly
1               5                   10

<210> SEQ ID NO 81
<211> LENGTH: 20
<212> TYPE: DNA
<213> ORGANISM: Homo sapiens
<220> FEATURE:
<223> OTHER INFORMATION: Type I GnRH Receptor forward primer

<400> SEQUENCE: 81
tgcctcttca tcatccctct                                           20

<210> SEQ ID NO 82
<211> LENGTH: 20
<212> TYPE: DNA
<213> ORGANISM: Homo sapiens
<220> FEATURE:
<223> OTHER INFORMATION: Type I GnRH Receptor reverse primer

<400> SEQUENCE: 82
gcaaatgcaa ccgtcatttt                                           20

<210> SEQ ID NO 83
<211> LENGTH: 20
<212> TYPE: DNA
<213> ORGANISM: Homo sapiens
<220> FEATURE:
<223> OTHER INFORMATION: Type II GnRH Receptor forward primer

<400> SEQUENCE: 83
actgttcaat ggctggctgt                                           20

<210> SEQ ID NO 84
<211> LENGTH: 20
<212> TYPE: DNA
<213> ORGANISM: Homo sapiens
<220> FEATURE:
<223> OTHER INFORMATION: Type II GnRH Receptor reverse primer

<400> SEQUENCE: 84
gcccccagaa gtttccttac                                           20

<210> SEQ ID NO 85
<211> LENGTH: 10
<212> TYPE: PRT
<213> ORGANISM: Artificial Sequence
<220> FEATURE:
<223> OTHER INFORMATION: Man-made anallogue of GnRH II

<400> SEQUENCE: 85

Glu His Trp Ser Tyr Trp Trp Tyr Pro Gly
1               5                   10

<210> SEQ ID NO 86
<211> LENGTH: 10

```
<212> TYPE: PRT
<213> ORGANISM: Artificial Sequence
<220> FEATURE:
<223> OTHER INFORMATION: Man-made analogue of GnRH II

<400> SEQUENCE: 86

Glu His Trp Ser Tyr Trp Trp Arg Pro Gly
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 87

Glu His Trp Ser His Trp Trp Tyr Pro Gly
1               5                   10

<210> SEQ ID NO 88
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 88

Glu His Trp Ser Tyr His Trp Arg Pro
1               5

<210> SEQ ID NO 89
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 89

Glu His Trp Ser His Trp Leu Arg Pro Gly
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 90

Glu His Trp Ser His Leu Trp Tyr Pro Gly
1               5                   10

<210> SEQ ID NO 91
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 91

Glu His Trp Ser His Leu Trp Tyr Pro
1               5

<210> SEQ ID NO 92
<211> LENGTH: 10
<212> TYPE: PRT
```

```
<213> ORGANISM: Artificial Sequence
<220> FEATURE:
<223> OTHER INFORMATION: Man-made analogue of GnRH II

<400> SEQUENCE: 92

Glu His Trp Ser His Ser Trp Tyr Pro Gly
1               5                   10

<210> SEQ ID NO 93
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 93

Glu His Trp Ser His Ser Trp Tyr Pro
1               5

<210> SEQ ID NO 94
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 94

Glu His Trp Ser His Trp Trp Tyr Pro Gly
1               5                   10

<210> SEQ ID NO 95
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 95

Glu His Trp Ser His Trp Trp Tyr Pro
1               5
```